US012648985B2

(12) United States Patent
Miller et al.

(10) Patent No.: US 12,648,985 B2
(45) Date of Patent: Jun. 9, 2026

(54) IMMUNOTHERAPEUTIC FOR PROSTATE CANCER TREATMENT

(71) Applicant: Hexamer Therapeutics, Inc., Pullman, WA (US)

(72) Inventors: Keith Douglas Miller, Moscow, ID (US); Robert Bogden, Viola, ID (US)

(73) Assignee: Hexamer Therapeutics, Inc., Pullman, WA (US)

( * ) Notice: Subject to any disclaimer, the term of this patent is extended or adjusted under 35 U.S.C. 154(b) by 1021 days.

(21) Appl. No.: 17/753,663

(22) PCT Filed: Sep. 10, 2020

(86) PCT No.: PCT/US2020/050194
§ 371 (c)(1),
(2) Date: Mar. 10, 2022

(87) PCT Pub. No.: WO2021/050722
PCT Pub. Date: Mar. 18, 2021

(65) Prior Publication Data
US 2022/0339238 A1 Oct. 27, 2022

Related U.S. Application Data

(60) Provisional application No. 62/899,553, filed on Sep. 12, 2019.

(51) Int. Cl.
| | |
|---|---|
| *A61K 38/09* | (2006.01) |
| *A61K 47/64* | (2017.01) |
| *A61P 13/08* | (2006.01) |
| *A61P 35/00* | (2006.01) |

(52) U.S. Cl.
CPC ........... *A61K 38/09* (2013.01); *A61K 47/646* (2017.08); *A61P 13/08* (2018.01); *A61P 35/00* (2018.01)

(58) Field of Classification Search
None
See application file for complete search history.

(56) References Cited

U.S. PATENT DOCUMENTS

| | | | | |
|---|---|---|---|---|
| 5,723,129 A | * | 3/1998 | Potter .................. | C07K 14/285 424/193.1 |
| 2006/0193853 A1 | | 8/2006 | Fuentes et al. | |
| 2017/0049883 A1 | | 2/2017 | Clegg et al. | |

FOREIGN PATENT DOCUMENTS

| | | | |
|---|---|---|---|
| EP | 2335736 | A1 | 6/2011 |
| JP | 2012504151 | A | 2/2012 |
| JP | 2022516126 | A | 2/2022 |
| WO | WO9715316 | A1 | 1/1997 |
| WO | WO9942472 | A1 | 8/1999 |
| WO | WO2015164798 | A1 | 10/2015 |
| WO | WO2018027252 | A1 | 2/2018 |
| WO | WO2020014609 | A2 | 1/2020 |
| WO | WO2021226026 | A2 | 11/2021 |

OTHER PUBLICATIONS

Burgess et al. (ACS Publications 2015, p. 10554-10562).*
Sad et al. (Immunology, 1991, vol. 74, p. 223-227).*
Extended European Search Report mailed Mar. 30, 2023 for European Patent Application No. 22203434.0, a corresponding foreign application of U.S. Appl. No. 17/753,663, 9 pages.
Truncaite et al., "Bacteriophage vB_EcoM_FV3: a new member of 'rV5-like viruses',", rArch Virol, Aug. 2012, 157:2431-2435.
Extended European Search Report mailed Jul. 3, 2023 for European Patent Application No. 20863353.7, a corresponding foreign application of U.S. Appl. No. 17/753,663, 8 pages.
Invitation to Pay Fees mailed Dec. 14, 2020 for Application PCT/US20/50194, "An Immunotherapeutic for Prostate Cancer Treatment", 3 pages.
International Search Report and Written Opinion mailed Feb. 19, 2021 for PCT Application No. PCT/US20/50194, 14 pages.
Office Action for Canadian Application No. 3, 152,055, Dated Sep. 8, 2023, 4 pages.
Office Action for Japanese Application No. 2022-516126, Dated Sep. 9, 2024, 16 pages.
Miller, et al., "Novel Anti-Nicotine Vaccine Using a Trimeric Coiled-Coil Hapten Carrier," PLOS One, vol. 9, No. 12, Dec. 2014, 19 pages.
Zeigler, et al., "Epitope Targeting with Self-Assembled Peptide Vaccines", NPJ Vaccines, vol. 4, No. 30, Jul. 2019, 8 pages.
Office Action for Chinese Application No. 202080062776.X, Dated Nov. 1, 2024, 26 pages.
Office Action for Canadian Application No. 3,152,055, Dated Apr. 30, 2025, 6 pages.
Office Action for Chinese Application No. 202080062776.X, Dated Apr. 30, 2025, 10 pages.
Exam Report for Australian Application No. 2020346818, Dated Jul. 14, 2025, 3 pages.
Office Action for Chinese Application No. 202080062776.X, dated Oct. 31, 2025, 12 pages.

(Continued)

*Primary Examiner* — Agnieszka Boesen
(74) *Attorney, Agent, or Firm* — Lee & Hayes, P.C.

(57) ABSTRACT

The present disclosure describes a GnRH therapeutic for neutralizing GnRH levels in subjects which can reduce testosterone levels to attenuate or eliminate prostate cancer cell growth and/or metastasis. The therapeutic is produced synthetically. The GnRH therapeutic includes a hapten carrier (hC) comprising a monomeric peptide (MP), synthesized separately from the GnRH peptide, and following self-assembly of the hC, GnRH is covalently coupled to form a GnRH-hC conjugate which can serve as a therapeutic. The MP includes heptad repeats following a specific pattern. The hC can include a GnRH peptide attached to a monomeric peptide prior to self-assembly to form a therapeutic. Optionally, the GnRH-hC conjugate further includes one or more T-cell epitopes at the N- and/or C-terminus of the one or more amphipathic alpha-helices. The present disclosure also describes compositions including immunogenic compositions including the therapeutics described herein.

31 Claims, 6 Drawing Sheets

Specification includes a Sequence Listing.

(56) References Cited

OTHER PUBLICATIONS

Office Action for Korean Application No. 10-2022-7012108, Dated Jan. 8, 2026, 26 pages.

Muyldermans, "Nanobodies: Natural Single-Domain Antibodies", Annual Review of Biochemistry, vol. 82, No. 1, Mar. 13, 2013, pp. 775-797.

Vincke, et al., "Generation of Single Domain Antibody Fragments Derived from Camelids and Generation of Manifold Constructs", Methods in Molecular Biology, Chapter 8, vol. 907, Aug. 2012, pp. 145-146, 153-170.

Office Action for Japanese Application No. 2025-076282, Dated Feb. 17, 2026, 11 pages.

* cited by examiner

Synthetic GnRH (~1.62 kDa)

carrier activation
and covalent coupling
of GnRH

-Residue # of monomer: 60
-Size of monomer: 6.5 kDa
-Size of self-assembled hexamer:   38.5 kDa
-Size of hexamer with 12 GnRH peptides: 55.7 kDa

*Fig. 3*
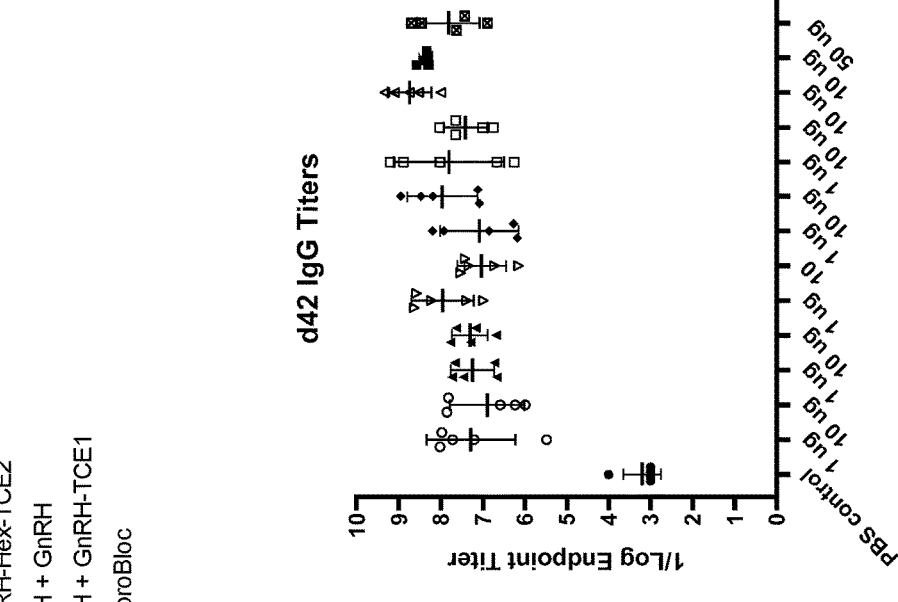
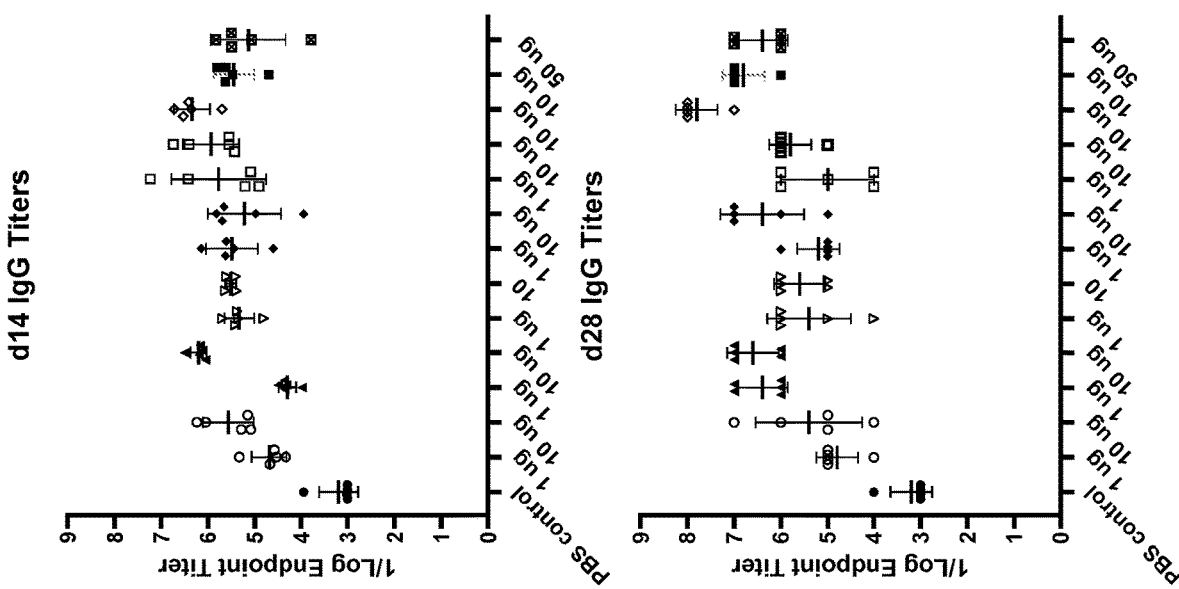

SEQUENCE LISTING

```
<160> NUMBER OF SEQ ID NOS: 78

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a hydrophobic or non-polar residue
<220> FEATURE:
<221> NAME/KEY: MISC_FEATURE
<222> LOCATION: (2)..(2)
<223> OTHER INFORMATION: Xaa is a positively charged, negatively
      charged, polar uncharged, or non-polar aliphatic residue
<220> FEATURE:
<221> NAME/KEY: MISC_FEATURE
<222> LOCATION: (3)..(3)
<223> OTHER INFORMATION: Xaa is a negatively charged, positively
      charged, non-polar aliphatic, polar uncharged residue or any
      natural or non-natural residue for epitope coupling to a hapten or
      any other molecule
<220> FEATURE:
<221> NAME/KEY: MISC_FEATURE
<222> LOCATION: (4)..(4)
```

-continued

```
<223> OTHER INFORMATION: Xaa is a hydrophobic or non-polar residue
<220> FEATURE:
<221> NAME/KEY: MISC_FEATURE
<222> LOCATION: (5)..(5)
<223> OTHER INFORMATION: Xaa is a negatively charged, positively
      charged, non-polar aliphatic, polar uncharged residue, or any
      natural or non-natural residue for epitope coupling to a hapten or
      any other molecule
<220> FEATURE:
<221> NAME/KEY: MISC_FEATURE
<222> LOCATION: (6)..(6)
<223> OTHER INFORMATION: Xaa is any natural or non-natural residue for
      epitope coupling to a hapten or any other molecule
<220> FEATURE:
<221> NAME/KEY: MISC_FEATURE
<222> LOCATION: (7)..(7)
<223> OTHER INFORMATION: Xaa is a negatively charged, positively
      charged, polar uncharged, non-polar aliphatic residue, or any
      natural or non-natural residue for epitope coupling to a hapten or
      any other molecule

<400> SEQUENCE: 1

Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: The sequence as a whole repeats n times,
      wherein n is an integer greater than 1
<220> FEATURE:
<221> NAME/KEY: MISC_FEATURE
<222> LOCATION: (1)..(1)
<223> OTHER INFORMATION: Xaa is a hydrophobic or non-polar residue
<220> FEATURE:
<221> NAME/KEY: MISC_FEATURE
<222> LOCATION: (2)..(2)
<223> OTHER INFORMATION: Xaa is a positively charged, negatively
      charged, polar uncharged, or non-polar aliphatic residue
<220> FEATURE:
<221> NAME/KEY: MISC_FEATURE
<222> LOCATION: (3)..(3)
<223> OTHER INFORMATION: Xaa is a negatively charged, positively
      charged, non-polar aliphatic, or polar uncharged residue
<220> FEATURE:
<221> NAME/KEY: MISC_FEATURE
<222> LOCATION: (4)..(4)
<223> OTHER INFORMATION: Xaa is a hydrophobic or non-polar residue
<220> FEATURE:
<221> NAME/KEY: MISC_FEATURE
<222> LOCATION: (5)..(5)
<223> OTHER INFORMATION: Xaa is a negatively charged, positively
      charged, non-polar aliphatic, or polar uncharged residue
<220> FEATURE:
<221> NAME/KEY: MISC_FEATURE
<222> LOCATION: (6)..(6)
<223> OTHER INFORMATION: Xaa is any natural or non-natural residue for
      epitope coupling
<220> FEATURE:
<221> NAME/KEY: MISC_FEATURE
<222> LOCATION: (7)..(7)
<223> OTHER INFORMATION: Xaa is a negatively charged, positively
      charged, polar uncharged, or non-polar aliphatic residue

<400> SEQUENCE: 2

Xaa Xaa Xaa Xaa Xaa Xaa Xaa
1               5

<210> SEQ ID NO 3
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Leu Arg Ser Ile Gly Lys Asp
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Leu Arg Ser Ile Gly Arg Asp
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Ile Arg Glu Ile Ser Arg Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Ile Arg Glu Val Ala Gln Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ile Arg Asp Ile Ala Lys Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Ile Arg Asp Ile Gly Arg Ala
1               5

<210> SEQ ID NO 9
<211> LENGTH: 7
```

<212> TYPE: PRT
<213> ORGANISM: Artificial Sequence
<220> FEATURE:
<223> OTHER INFORMATION: Synthetic peptide

<400> SEQUENCE: 9

Ile Arg Asp Val Gly Gln Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Ile Arg Asp Leu Ala Lys Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Val Lys Asp Val Ala Arg Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Ile Arg Asp Ile Gly Asn Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Ile Lys Asp Leu Ala Arg Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Ile Lys Lys Leu Lys Lys Lys
1               5

<210> SEQ ID NO 15
<211> LENGTH: 7
<212> TYPE: PRT

```
<213> ORGANISM: Artificial Sequence
<220> FEATURE:
<223> OTHER INFORMATION: Synthetic peptide

<400> SEQUENCE: 15

Ile Arg Ser Ile Gly Lys Glu
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Ile Arg Ser Ile Gly Arg Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Ile Lys Ser Ile Gly Arg Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Ile Arg Ser Ile Gly Arg Gly
1               5

<210> SEQ ID NO 19
<211> LENGTH: 28
<212> TYPE: PRT
<213> ORGANISM: Artificial Sequence
<220> FEATURE:
<223> OTHER INFORMATION: Synthetic peptide

<400> SEQUENCE: 19

Leu Arg Ser Ile Gly Lys Asp Leu Arg Ser Ile Gly Lys Asp Leu Arg
1               5                   10                  15

Ser Ile Gly Lys Asp Leu Arg Ser Ile Gly Lys Asp
            20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic peptide

<400> SEQUENCE: 20

Leu Arg Ser Ile Gly Lys Asp Leu Arg Ser Ile Gly Lys Asp Leu Arg
1               5                   10                  15

Ser Ile Gly Lys Asp Leu Arg Ser Ile Gly Lys Asp Ser
            20                  25
```

-continued

```
<210> SEQ ID NO 21
<211> LENGTH: 28
<212> TYPE: PRT
<213> ORGANISM: Artificial Sequence
<220> FEATURE:
<223> OTHER INFORMATION: Synthetic peptide

<400> SEQUENCE: 21

Leu Arg Ser Ile Gly Lys Asp Leu Arg Ser Ile Gly Arg Asp Leu Arg
1               5                   10                  15

Ser Ile Gly Lys Asp Leu Arg Ser Ile Gly Arg Asp
            20                  25

<210> SEQ ID NO 22
<211> LENGTH: 28
<212> TYPE: PRT
<213> ORGANISM: Artificial Sequence
<220> FEATURE:
<223> OTHER INFORMATION: Synthetic peptide

<400> SEQUENCE: 22

Ile Arg Glu Ile Ser Arg Ala Ile Arg Glu Val Ala Gln Ser Ile Arg
1               5                   10                  15

Asp Ile Ala Lys Ala Ile Arg Glu Ile Gly Lys Ser
            20                  25

<210> SEQ ID NO 23
<211> LENGTH: 28
<212> TYPE: PRT
<213> ORGANISM: Artificial Sequence
<220> FEATURE:
<223> OTHER INFORMATION: Synthetic peptide

<400> SEQUENCE: 23

Ile Arg Asp Ile Gly Arg Ala Ile Arg Asp Val Gly Gln Ser Ile Arg
1               5                   10                  15

Asp Leu Ala Lys Gly Ile Arg Asp Ile Ser Lys Gly
            20                  25

<210> SEQ ID NO 24
<211> LENGTH: 28
<212> TYPE: PRT
<213> ORGANISM: Artificial Sequence
<220> FEATURE:
<223> OTHER INFORMATION: Synthetic peptide

<400> SEQUENCE: 24

Val Lys Asp Val Ala Arg Gly Ile Arg Asp Ile Gly Asn Ser Ile Lys
1               5                   10                  15

Asp Leu Ala Arg Gly Ile Arg Asp Ile Gly Arg Gly
            20                  25

<210> SEQ ID NO 25
<211> LENGTH: 28
<212> TYPE: PRT
<213> ORGANISM: Artificial Sequence
<220> FEATURE:
<223> OTHER INFORMATION: monomeric hC peptides

<400> SEQUENCE: 25

Ile Arg Ser Ile Gly Lys Glu Ile Arg Ser Ile Gly Arg Glu Ile Lys
1               5                   10                  15

Ser Ile Gly Arg Glu Ile Arg Ser Ile Gly Arg Gly
```

```
                20              25

<210> SEQ ID NO 26
<211> LENGTH: 28
<212> TYPE: PRT
<213> ORGANISM: Artificial Sequence
<220> FEATURE:
<223> OTHER INFORMATION: monomeric hC peptides

<400> SEQUENCE: 26

Ile Arg Ser Ile Gly Lys Glu Ile Arg Ser Ile Gly Arg Glu Ile Arg
1               5                   10                  15

Ser Ile Gly Lys Glu Ile Arg Ser Ile Gly Arg Glu
            20              25

<210> SEQ ID NO 27
<211> LENGTH: 28
<212> TYPE: PRT
<213> ORGANISM: Artificial Sequence
<220> FEATURE:
<223> OTHER INFORMATION: monomeric hC peptides

<400> SEQUENCE: 27

Ile Arg Ser Ile Gly Lys Glu Ile Arg Ser Ile Gly Arg Glu Ile Arg
1               5                   10                  15

Ser Ile Gly Arg Glu Ile Arg Ser Ile Gly Arg Glu
            20              25

<210> SEQ ID NO 28
<211> LENGTH: 10
<212> TYPE: PRT
<213> ORGANISM: Artificial Sequence
<220> FEATURE:
<223> OTHER INFORMATION: GnRH peptide sequence pattern
<220> FEATURE:
<221> NAME/KEY: MISC_FEATURE
<222> LOCATION: (1)..(1)
<223> OTHER INFORMATION: Xaa ia a polar or charged amino acid
<220> FEATURE:
<221> NAME/KEY: MISC_FEATURE
<222> LOCATION: (5)..(5)
<223> OTHER INFORMATION: Xaa ia a polar amino acid
<220> FEATURE:
<221> NAME/KEY: MISC_FEATURE
<222> LOCATION: (7)..(7)
<223> OTHER INFORMATION: Xaa ia a hydrophobic or amphipathic amino acid
<220> FEATURE:
<221> NAME/KEY: MISC_FEATURE
<222> LOCATION: (8)..(8)
<223> OTHER INFORMATION: Xaa ia a hydrophobic, amphipathic, charged, or
      polar amino acid

<400> SEQUENCE: 28

Xaa His Trp Ser Xaa Gly Xaa Xaa Pro Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: GnRH peptide

<400> SEQUENCE: 29

Gln His Trp Ser Tyr Gly Leu Arg Pro Gly
1               5                   10

<210> SEQ ID NO 30
```

```
<211> LENGTH: 10
<212> TYPE: PRT
<213> ORGANISM: Artificial Sequence
<220> FEATURE:
<223> OTHER INFORMATION: GnRH peptide

<400> SEQUENCE: 30

Gln His Trp Ser His Gly Trp Leu Pro Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: GnRH peptide

<400> SEQUENCE: 31

Glu His Trp Ser Tyr Gly Leu Arg Pro Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: GnRH peptide

<400> SEQUENCE: 32

Gln His Trp Ser Tyr Gly Trp Tyr Pro Gly
1               5                   10

<210> SEQ ID NO 33
<211> LENGTH: 10
<212> TYPE: PRT
<213> ORGANISM: Artificial Sequence
<220> FEATURE:
<223> OTHER INFORMATION: GnRH peptide

<400> SEQUENCE: 33

Glu His Trp Ser Tyr Gly Leu Gln Pro Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: GnRH peptide

<400> SEQUENCE: 34

Gln His Trp Ser His Gly Trp Tyr Pro Gly
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is Gly or Val

<400> SEQUENCE: 35

Xaa Gln His Trp Ser Tyr Gly Leu Arg Pro Gly
1               5                   10
```

```
<210> SEQ ID NO 36
<211> LENGTH: 4
<212> TYPE: PRT
<213> ORGANISM: Artificial Sequence
<220> FEATURE:
<223> OTHER INFORMATION: Synthetic peptide

<400> SEQUENCE: 36

Gly Glu Asp Cys
1

<210> SEQ ID NO 37
<211> LENGTH: 5
<212> TYPE: PRT
<213> ORGANISM: Artificial Sequence
<220> FEATURE:
<223> OTHER INFORMATION: residues of GnRH peptides

<400> SEQUENCE: 37

Asp Gly Glu Gly Cys
1               5

<210> SEQ ID NO 38
<211> LENGTH: 15
<212> TYPE: PRT
<213> ORGANISM: Clostridium botulinum

<400> SEQUENCE: 38

Leu Leu Val Leu Val Phe Thr Phe Ser Leu Ile Ile Ser Ala Ser
1               5                   10                  15

<210> SEQ ID NO 39
<211> LENGTH: 15
<212> TYPE: PRT
<213> ORGANISM: Clostridium botulinum

<400> SEQUENCE: 39

Phe Ser Leu Ile Ile Ser Ala Ser Ser Ala Asn Gln Val Tyr Ala
1               5                   10                  15

<210> SEQ ID NO 40
<211> LENGTH: 15
<212> TYPE: PRT
<213> ORGANISM: Clostridium perfringens

<400> SEQUENCE: 40

Arg Leu Ile Thr Ala Met Ile Leu Ala Gly Ala Ile Ser Ile Gly
1               5                   10                  15

<210> SEQ ID NO 41
<211> LENGTH: 15
<212> TYPE: PRT
<213> ORGANISM: Staphylococcus aureus

<400> SEQUENCE: 41

Asn Arg Asn Phe Leu Gln Arg Ile Trp Asp Ala Ile Val Ala Phe
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Mycobacterium
```

-continued

<400> SEQUENCE: 42

```
Thr Pro Ser Thr Asp Ser Thr Ala Phe Thr Ala Val Ala Gln Glu
1               5                   10                  15
```

<210> SEQ ID NO 43
<211> LENGTH: 15
<212> TYPE: PRT
<213> ORGANISM: Artificial Sequence
<220> FEATURE:
<223> OTHER INFORMATION: Mycobacterium

<400> SEQUENCE: 43

```
Arg Gly Gln Phe Asp Arg Phe Thr Arg Asp Thr Gly Ile Ala Val
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Mycobacterium

<400> SEQUENCE: 44

```
Gly Gln Phe Asp Arg Phe Thr Arg Asp Thr Gly Ile Ala Val Asn
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Mycobacterium

<400> SEQUENCE: 45

```
Phe Thr Arg Asp Thr Gly Ile Ala Val Asn Leu Val Glu Ala Gly
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Mycobacterium

<400> SEQUENCE: 46

```
Val Ile Gly Leu Ala Ala Val Thr Ile Ala Ala Ala Ala Thr Ala
1               5                   10                  15
```

<210> SEQ ID NO 47
<211> LENGTH: 15
<212> TYPE: PRT
<213> ORGANISM: Clostridium tetani

<400> SEQUENCE: 47

```
Ile Glu Ile Ile Asp Ser Leu Gln Trp Asp Arg Asn Leu Arg Ile
1               5                   10                  15
```

<210> SEQ ID NO 48
<211> LENGTH: 15
<212> TYPE: PRT
<213> ORGANISM: Clostridium tetani

<400> SEQUENCE: 48

```
Glu Ile Ile Asp Ser Leu Gln Trp Asp Arg Asn Leu Arg Ile Asn
1               5                   10                  15
```

```
<210> SEQ ID NO 49
<211> LENGTH: 15
<212> TYPE: PRT
<213> ORGANISM: Clostridium tetani

<400> SEQUENCE: 49

Ile Ile Asp Ser Leu Gln Trp Asp Arg Asn Leu Arg Ile Asn Leu
1               5                   10                  15

<210> SEQ ID NO 50
<211> LENGTH: 15
<212> TYPE: PRT
<213> ORGANISM: Mycobacterium tuberculosis

<400> SEQUENCE: 50

Glu Ile Ser Thr Asn Ile Arg Gln Ala Gly Val Gln Tyr Ser Arg
1               5                   10                  15

<210> SEQ ID NO 51
<211> LENGTH: 20
<212> TYPE: PRT
<213> ORGANISM: Mycobacterium tuberculosis

<400> SEQUENCE: 51

Ser Glu Phe Ala Tyr Gly Ser Phe Val Arg Thr Val Ser Leu Pro Val
1               5                   10                  15

Gly Ala Asp Glu
            20

<210> SEQ ID NO 52
<211> LENGTH: 15
<212> TYPE: PRT
<213> ORGANISM: Mumps virus

<400> SEQUENCE: 52

Gly Thr Tyr Arg Leu Ile Pro Asn Ala Arg Ala Asn Leu Thr Ala
1               5                   10                  15

<210> SEQ ID NO 53
<211> LENGTH: 16
<212> TYPE: PRT
<213> ORGANISM: Plasmodium falciparum

<400> SEQUENCE: 53

Glu Glu Asn Val Glu Glu Asn Val Glu Glu Asn Val Glu Glu Asn Val
1               5                   10                  15

<210> SEQ ID NO 54
<211> LENGTH: 20
<212> TYPE: PRT
<213> ORGANISM: Human immunodeficiency virus type 1

<400> SEQUENCE: 54

Ala Phe Ser Pro Glu Val Ile Pro Met Phe Ser Ala Leu Ser Glu Gly
1               5                   10                  15

Ala Thr Pro Gln
            20

<210> SEQ ID NO 55
<211> LENGTH: 21
<212> TYPE: PRT
<213> ORGANISM: Hepatitis C virus

<400> SEQUENCE: 55
```

-continued

```
Gly Glu Gly Ala Val Gln Trp Met Asn Arg Leu Ile Ala Phe Ala Ser
1               5                   10                  15

Arg Gly Asn His Val
            20

<210> SEQ ID NO 56
<211> LENGTH: 11
<212> TYPE: PRT
<213> ORGANISM: Influenza A virus

<400> SEQUENCE: 56

Phe Val Phe Thr Leu Thr Val Pro Ser Glu Arg
1               5                   10

<210> SEQ ID NO 57
<211> LENGTH: 20
<212> TYPE: PRT
<213> ORGANISM: Influenza A virus

<400> SEQUENCE: 57

Leu Val Val Pro Arg Tyr Ala Phe Ala Met Glu Arg Asn Ala Gly Ser
1               5                   10                  15

Gly Ile Ile Ile
            20

<210> SEQ ID NO 58
<211> LENGTH: 7
<212> TYPE: PRT
<213> ORGANISM: Artificial Sequence
<220> FEATURE:
<223> OTHER INFORMATION: TLR-4 agonist

<400> SEQUENCE: 58

Ala Pro Pro His Ala Leu Ser
1               5

<210> SEQ ID NO 59
<211> LENGTH: 19
<212> TYPE: PRT
<213> ORGANISM: Artificial Sequence
<220> FEATURE:
<223> OTHER INFORMATION: TCE1

<400> SEQUENCE: 59

Leu Thr Ala Glu Leu Lys Ile Tyr Ser Val Ile Gln Ala Glu Ile Asn
1               5                   10                  15

Lys His Leu

<210> SEQ ID NO 60
<211> LENGTH: 23
<212> TYPE: PRT
<213> ORGANISM: Artificial Sequence
<220> FEATURE:
<223> OTHER INFORMATION: TCE2

<400> SEQUENCE: 60

Phe Asn Asn Phe Thr Val Ser Phe Trp Leu Arg Val Pro Arg Val Ser
1               5                   10                  15

Ala Ser His Leu Glu Gln Tyr
            20

<210> SEQ ID NO 61
<211> LENGTH: 14
```

-continued

```
<212> TYPE: PRT
<213> ORGANISM: Artificial Sequence
<220> FEATURE:
<223> OTHER INFORMATION: TCE3

<400> SEQUENCE: 61

Gly Gln Glu Ala Phe Ser His Ile Arg Ile Pro Leu Pro His
1               5                   10

<210> SEQ ID NO 62
<211> LENGTH: 15
<212> TYPE: PRT
<213> ORGANISM: Artificial Sequence
<220> FEATURE:
<223> OTHER INFORMATION: TCE4

<400> SEQUENCE: 62

Phe Gln Asp Ala Tyr Asn Ala Ala Gly Gly His Asn Ala Val Phe
1               5                   10                  15

<210> SEQ ID NO 63
<211> LENGTH: 4
<212> TYPE: PRT
<213> ORGANISM: Artificial Sequence
<220> FEATURE:
<223> OTHER INFORMATION: Synthesized

<400> SEQUENCE: 63

Gly Pro Gly Pro
1

<210> SEQ ID NO 64
<211> LENGTH: 5
<212> TYPE: PRT
<213> ORGANISM: Artificial Sequence
<220> FEATURE:
<223> OTHER INFORMATION: Synthesized

<400> SEQUENCE: 64

Gly Pro Gly Pro Gly
1               5

<210> SEQ ID NO 65
<211> LENGTH: 6
<212> TYPE: PRT
<213> ORGANISM: Artificial Sequence
<220> FEATURE:
<223> OTHER INFORMATION: Synthesized

<400> SEQUENCE: 65

Gly Pro Gly Pro Gly Cys
1               5

<210> SEQ ID NO 66
<211> LENGTH: 6
<212> TYPE: PRT
<213> ORGANISM: Artificial Sequence
<220> FEATURE:
<223> OTHER INFORMATION: Synthesized

<400> SEQUENCE: 66

Ser Gly Pro Gly Pro Gly
1               5

<210> SEQ ID NO 67
<211> LENGTH: 67
<212> TYPE: PRT
```

<213> ORGANISM: Artificial Sequence
<220> FEATURE:
<223> OTHER INFORMATION: GnRH_Hex_TCE2

<400> SEQUENCE: 67

Gly Gln His Trp Ser Tyr Gly Leu Arg Pro Gly Gly Asp Ile Arg Ser
1               5                   10                  15

Ile Gly Lys Glu Ile Arg Ser Ile Gly Arg Glu Ile Lys Ser Ile Gly
                20                  25                  30

Arg Glu Ile Arg Ser Ile Gly Arg Gly Pro Gly Pro Phe Asn Asn Phe
            35                  40                  45

Thr Val Ser Phe Trp Leu Arg Val Pro Arg Val Ser Ala Ser His Leu
        50                  55                  60

Glu Gln Tyr
65

<210> SEQ ID NO 68
<211> LENGTH: 58
<212> TYPE: PRT
<213> ORGANISM: Artificial Sequence
<220> FEATURE:
<223> OTHER INFORMATION: TCE3_Hex_TCE4

<400> SEQUENCE: 68

Gly Gln Glu Ala Phe Ser His Ile Arg Ile Pro Leu Pro His Asp Ile
1               5                   10                  15

Arg Ser Ile Gly Lys Glu Ile Arg Ser Ile Gly Arg Glu Ile Arg Ser
                20                  25                  30

Ile Gly Lys Glu Ile Arg Ser Ile Gly Arg Glu Phe Gln Asp Ala Tyr
            35                  40                  45

Asn Ala Ala Gly Gly His Asn Ala Val Phe
        50                  55

<210> SEQ ID NO 69
<211> LENGTH: 56
<212> TYPE: PRT
<213> ORGANISM: Artificial Sequence
<220> FEATURE:
<223> OTHER INFORMATION: GnRH_Hex_GnRH

<400> SEQUENCE: 69

Gly Gln His Trp Ser Tyr Gly Leu Arg Pro Gly Gly Ser Gly Asp Ile
1               5                   10                  15

Arg Ser Ile Gly Lys Glu Ile Arg Ser Ile Gly Arg Glu Ile Arg Ser
                20                  25                  30

Ile Gly Arg Glu Ile Arg Ser Ile Gly Arg Glu Gly Ser Gly Gln His
            35                  40                  45

Trp Ser Tyr Gly Leu Arg Pro Gly
        50                  55

<210> SEQ ID NO 70
<211> LENGTH: 15
<212> TYPE: PRT
<213> ORGANISM: Artificial Sequence
<220> FEATURE:
<223> OTHER INFORMATION: GnRH

<400> SEQUENCE: 70

Gln His Trp Ser Tyr Gly Leu Arg Pro Gly Asp Gly Glu Gly Cys
1               5                   10                  15

```
<210> SEQ ID NO 71
<211> LENGTH: 57
<212> TYPE: PRT
<213> ORGANISM: Artificial Sequence
<220> FEATURE:
<223> OTHER INFORMATION: GnRH_TCE1

<400> SEQUENCE: 71

Gln His Trp Ser Tyr Gly Leu Arg Pro Gly Ser Gly Pro Gly Pro Gly
1               5                   10                  15

Leu Thr Ala Glu Leu Lys Ile Tyr Ser Val Ile Gln Ala Glu Ile Asn
            20                  25                  30

Lys His Leu Gly Pro Gly Pro Gly Ser Phe Glu Arg Phe Glu Ile Phe
        35                  40                  45

Pro Lys Glu Gly Pro Gly Pro Gly Cys
    50                  55

<210> SEQ ID NO 72
<211> LENGTH: 14
<212> TYPE: PRT
<213> ORGANISM: Artificial Sequence
<220> FEATURE:
<223> OTHER INFORMATION: GnRH peptide with synthetic peptide

<400> SEQUENCE: 72

Gln His Trp Ser Tyr Gly Leu Arg Pro Gly Gly Glu Asp Cys
1               5                   10

<210> SEQ ID NO 73
<211> LENGTH: 14
<212> TYPE: PRT
<213> ORGANISM: Artificial Sequence
<220> FEATURE:
<223> OTHER INFORMATION: GnRH peptide with synthetic peptide

<400> SEQUENCE: 73

Gln His Trp Ser His Gly Trp Leu Pro Gly Gly Glu Asp Cys
1               5                   10

<210> SEQ ID NO 74
<211> LENGTH: 14
<212> TYPE: PRT
<213> ORGANISM: Artificial Sequence
<220> FEATURE:
<223> OTHER INFORMATION: GnRH peptide with synthetic peptide

<400> SEQUENCE: 74

Glu His Trp Ser Tyr Gly Leu Arg Pro Gly Gly Glu Asp Cys
1               5                   10

<210> SEQ ID NO 75
<211> LENGTH: 14
<212> TYPE: PRT
<213> ORGANISM: Artificial Sequence
<220> FEATURE:
<223> OTHER INFORMATION: GnRH peptide with synthetic peptide

<400> SEQUENCE: 75

Gln His Trp Ser Tyr Gly Trp Tyr Pro Gly Gly Glu Asp Cys
1               5                   10

<210> SEQ ID NO 76
<211> LENGTH: 14
<212> TYPE: PRT
<213> ORGANISM: Artificial Sequence
<220> FEATURE:
```

-continued

```
<223> OTHER INFORMATION: GnRH peptide with synthetic peptide

<400> SEQUENCE: 76

Glu His Trp Ser Tyr Gly Leu Gln Pro Gly Gly Glu Asp Cys
1               5                   10

<210> SEQ ID NO 77
<211> LENGTH: 14
<212> TYPE: PRT
<213> ORGANISM: Artificial Sequence
<220> FEATURE:
<223> OTHER INFORMATION: GnRH peptide with synthetic peptide

<400> SEQUENCE: 77

Gln His Trp Ser His Gly Trp Tyr Pro Gly Gly Glu Asp Cys
1               5                   10

<210> SEQ ID NO 78
<211> LENGTH: 11
<212> TYPE: PRT
<213> ORGANISM: Artificial Sequence
<220> FEATURE:
<223> OTHER INFORMATION: TCE1

<400> SEQUENCE: 78

Ser Phe Glu Arg Phe Glu Ile Phe Pro Lys Glu
1               5                   10
```

IMMUNOTHERAPEUTIC FOR PROSTATE CANCER TREATMENT

CROSS REFERENCE TO RELATED APPLICATIONS

This application is a U.S. National phase application of International Application No. PCT/US/2020/050194, filed Sep. 10, 2020, which claims the benefit of U.S. Provisional Patent Application 62/899,553, filed on Sep. 12, 2019, which is are hereby incorporated by reference in its entirety.

SEQUENCE LISTING INFORMATION

A computer readable text file, entitled "H197-0005PCT_ST25.txt," created on or about Sep. 9, 2020, with a file size of about 22 KB, contains the sequence listing for this application and is hereby incorporated by reference in its entirety.

TECHNICAL FIELD

The present disclosure describes the synthesis of a peptide-based prostate cancer therapeutic.

BACKGROUND

In patients with advanced prostate cancer, it is critically important to minimize the amount of testosterone in the body (to prevent the advancement and spread of prostate cancer cells). There are several FDA approved drugs on the market that decrease testosterone in male humans: Lupron injection (leuprolide acetate, a gonadotropin releasing hormone (GnRH) agonist) and Firmagon (degarelix, a GnRH antagonist). Both of these powerful drugs have significant adverse side effects, and in some instances contribute to additional serious health problems for the patient. Accordingly, there is a need to develop improved drugs with reduced side effects for treating patients with prostate cancer.

Recombinant protein expression in hosts such as bacteria (predominantly *E. coli*), yeast, insect cells, and mammalian cells is currently the most common method of producing subunit therapeutics. It has been very successful and will remain an important method of therapeutic production. Typically, a target protein is identified by genomics analysis, functional assays, in silico analyses (e.g. functional prediction, structural analysis, epitope identification, etc.), or a combination of the three. Expression trials are initiated to assess yield and solubility for immunogenicity trials. Subunits producing high-titer antibodies to the disease target are then carried forward to assess function where the therapeutic is tested for its ability to protect hosts against disease manifestation and progression. Subunits meeting all these criteria are then moved forward for therapeutic production optimization, stability, and toxicity/safety/dosage studies. Expression optimization studies are also important to determine production scale and feasibility. It is well known that the entire process is time consuming, labor intensive, and very costly.

Therefore, there is also a need to develop a more efficient and cost-effective method to produce therapeutics for treating prostate cancer.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The present disclosure describes a hMP polypeptide including a hapten (h) attached to a monomeric peptide (MP). The present disclosure also describes a conjugate including a hapten conjugated to a hapten carrier (hC). The hapten can be a target protein or target antigen. In embodiments, the hapten is a GnRH peptide; the hMP polypeptide includes GnRH (G) and a MP (GMP); and the conjugate is GnRH-hC. In embodiments, the hMP can function as a hC or an oligomer hC, such as HhC (hexamer hC), after self-assembly, because it can adopt the same secondary, tertiary or quaternary structure. In embodiments, when the T-cell epitopes are attached to the MP in addition to a hapten, for example GnRH, the GMP can function similar to a GnRH-hC conjugate, but without the conjugated GnRH. In embodiments, the GnRH peptide includes an amino acid sequence as set forth in SEQ ID NOs: 28-34.

The hC described herein includes monomeric peptides that are amphipathic alpha-helices comprising two or more heptad repeats that self-assemble into a dimer, trimer, tetramer, pentamer, hexamer, heptamer, octamer, nanomer, or decamer. Each of the heptads comprises an amino acid sequence as set forth in SEQ ID NO: 1-18. In embodiments, the monomeric peptides self-assemble into a hexameric hapten carrier (HhC). The hC can also include a target antigen, such as GnRH, in which case the hC is GMP that has self-assembled into an oligomer (GhC oligomer). In embodiments, the GMP self-assembles into a hexamer, for example, an hC including GnRH peptide joined to a HhC (GHhC). In embodiments, the conjugate described herein includes GnRH conjugated to the HhC (GnRH-HhC).

Moreover, the present disclosure describes GhC oligomer or conjugates of GnRH-hC containing T-cell epitopes at the N- and/or C-termini of the amphipathic alpha-helices of the hC that are part of the monomeric peptide, or that were covalently attached to either GhC or GnRH-hC.

In embodiments, the present disclosure describes compositions comprising the GnRH-hC conjugates or GhC oligomers described herein and an excipient. In embodiments, the composition is a pharmaceutical composition, which can be used to treat subjects in need thereof. The pharmaceutical composition can be an immunogenic composition. The subject could be suffering from a disease or condition, for example, prostate cancer. The subject may need to have reduced testosterone levels so that prostate tumor cells do not proliferate or metastasize. In embodiments, the pharmaceutical compositions or the GnRH-hC conjugates or GhC oligomers can be used as therapeutics for treating prostate cancer.

In embodiments, the present disclosure describes methods of using the GnRH-hC conjugates or GhC oligomers described herein as therapeutics, such as an immunogen, to induce a robust and long-lasting immune response in subjects requiring reduced testosterone levels.

BRIEF DESCRIPTION OF THE DRAWINGS

FIG. 3 shows mouse anti-GnRH IgG titers at d14 (day 14), d28, and d42 induced by exemplary GnRH-HhC conjugates and a GHhC oligomer compared to controls.

DETAILED DESCRIPTION

Figure 1:
FIG. 1 shows the synthesis of the GnRH-hC conjugate. Lysines were initially activated with a heterobifunctional cross-linker that reacts with the hC lysine and then the C-terminal cysteine of GnRH to form the GnRH-hC conjugate. This reaction was performed with a large excess (>10 molar equivalents) of cross linker and GnRH to ensure the hC is fully loaded (12 covalently attached GnRH peptides are shown here). A tryptophan in GnRH allows quantifying coupling efficiency by fluorescence spectroscopy. The N- and C-termini of the HhC contain T-cell epitopes added during solid phase peptide synthesis (SPPS).

Haptens are small molecules that lack antigenic determinants due to their small size. In order to become antigenic, they must be coupled to a larger carrier protein to be immunogenic. As used herein, the term "hapten" refers to any molecule that lacks antigenic determinants until it is covalently or non-covalently attached to a larger carrier protein, or a molecule whose antigenicity is increased by covalently or non-covalently coupling to a larger carrier protein. Similar to haptens, small peptides (i.e. usually those less than 5,000 Daltons) also lack antigenic determinants to induce a robust immune response, so they too must be coupled to a larger carrier protein to be immunogenic. Accordingly, the term "haptens" refers to molecules that are not good immunogens by themselves, but they become immunogenic when attached to a larger molecule. A hapten can be a small organic molecule, a monosaccharide, disaccharide, oligosaccharide, a lipid, nucleic acid, peptide, or a polypeptide, for example. Although a hapten may be capable of binding to an antibody, immunization with a hapten does not usually provoke a strong antibody response. However, immunogenicity can be achieved when the hapten is covalently attached by linking or conjugating to a larger carrier molecule, such as a hapten-carrier conjugate that is greater than 5,000 Daltons.

The present disclosure describes hapten carrier (hC) for small peptides, such as GnRH. When GnRH is conjugated to a hC described herein, GnRH can induce a robust immune response.

GnRH is a 10-residue peptide produced in the hypothalamus of vertebrates. It induces the pituitary gland to synthesize and secrete luteinizing hormone (LH) and follicle-stimulating hormone (FSH). In males, these hormones cause the testes to make testosterone, and in females, they cause the ovaries to make estrogen and progesterone. Thus, antibodies induced by vaccination with GnRH neutralize it and prevent it from binding to its receptor and block testosterone production.

The present disclosure also describes therapeutics including a GnRH-hC conjugate comprising GnRH covalently attached to the hC described herein and a GhC oligomer comprising GnRH and a monomeric peptide. The GhC oligomer can also include T-cell epitopes. In this manner, the GnRH therapeutics, which include both GnRH-hC and GhC, can induce a robust and long-lasting immune response via the adaptive immune response pathway to make high titer and high affinity antibodies targeting endogenous GnRH, preventing the release of LH (Luteinizing Hormone), and drastically reducing testosterone production. As an example, the GnRH can induce a robust and long-lasting immune response through T-cell activation, dendritic cell maturation, B-cell activation, proliferation, and maturation, establishment of a robust memory response, and other pathways. This ultimately results in neutralizing GnRH before it leaves the hypothalamus and enters the portal vessels en route to the pituitary, which controls adrenal and gonadal testosterone production.

After an initial prime/boost in humans, it is expected that the testosterone levels to be <0.7 (ng/dL) and maintained below that level with one or two annual "booster shots". The side effects of the therapeutic will be minimal due to the presence of a precise number of well characterized T-cell epitopes, the lack of immunodominant epitopes on the hC, and the completely synthetic (non-biological) production of the therapeutic. The precise spatial and stoichiometric placement of multiple conformational and linear GnRH B-cell epitopes on the carrier will result in a potent therapeutic capable of attenuating testosterone superior to existing drugs.

Moreover, the present disclosure describes a novel method for producing GnRH therapeutics including a GnRH-hC conjugate or a GhC oligomer. The method eliminates many of the costliest and time-consuming steps of traditional subunit or protein carrier-based therapeutic development. Instead of producing carrier proteins in recombinant expression hosts, a flexible and modular system where the hC and GnRH components are produced synthetically by solid phase peptide synthesis (SPPS). The method described herein includes designing a hC component including monomeric peptides that self-assemble into amphipathic alpha-helices to form a carrier complex large enough to induce a robust immune response after one or more GnRH peptides are attached to the hC. In embodiments, the monomeric peptides self-assemble into a hexameric hC (HhC) core, and the GnRH peptides can be covalently attached to the HhC core, either at the N- or C-terminus of the monomeric peptide prior to self-assembly into a hexamer or conjugated to the HhC core after self-assembly into a hexamer. In embodiments, the HhC core can also include T-cell epitopes at the N- and/or C-terminus of the amphipathic alpha-helices.

As an example, FIG. 1 shows the components of the GnRH-HhC conjugate described herein. There is a central region which forms the core following hydration, and lysines in this region function for conjugating GnRH. The size of the HhC can vary according to T-cell epitope length. Upon hexamer formation, the unconjugated hexamer is 38.5 kDa (FIG. 1). The conjugated hexamer can vary depending on the length and size of the conjugated hapten. For example, GnRH (1,200 Daltons) loaded onto the hexamer would increase the size from 38.5 kDa to about 53 kDa.

The present disclosure describes a core region of the hC that includes a peptide of at least 14 amino acid residues long and comprising at least two heptad repeats, each heptad having the pattern hwxhxyz (SEQ ID NO: 1), wherein h is a hydrophobic or non-polar residue;

w is a positively charged, negatively charged, polar uncharged, or non-polar aliphatic residue;

x is negatively charged, positively charged, non-polar aliphatic, polar uncharged residue, or any natural or non-natural residue for epitope coupling to a hapten or any other molecule;

y is any natural or non-natural residue for epitope coupling to a hapten or any other molecule; and z is a negatively charged, positively charged, polar uncharged, non-polar aliphatic residue, or any natural or non-natural residue for epitope coupling to a hapten or any other molecule.

In embodiments, the hC core region includes a peptide having the pattern (hwxhxyz)n (SEQ ID NO: 2), wherein h is I, L, V, F, W, Y, M, W, G, or A;

w is G, R, A, N, Q, H, S, D, E, K or T;

x is R, S, N, Q, A, G, T, D, E, K, H, or C;

y is K, H, C, D, E, R, W, Y, Q, N, or a non-natural amino acid or molecule containing reactive groups amenable to covalent coupling;

Z is A, D, H, S, E, R, N, Q, K, or G; and n is an integer greater than 1

In embodiments, the exemplary heptads described herein have the following amino acid sequences:

```
                            (SEQ ID NO: 3)
LRSIGKD;

(SEQ ID NO: 4)
LRSIGRD;

(SEQ ID NO: 5)
IREISRA;

(SEQ ID NO: 6)
IREVAQS;

(SEQ ID NO: 7)
IRDIAKA;

(SEQ ID NO: 8)
IRDIGRA;

(SEQ ID NO: 9)
IRDVGQS;

(SEQ ID NO: 10)
IRDLAKG;

(SEQ ID NO: 11)
VKDVARG;

(SEQ ID NO: 12)
IRDIGNS;

(SEQ ID NO: 13)
IKDLARG;

(SEQ ID NO: 14)
IKKLKKK;

(SEQ ID NO: 15)
IRSIGKE;

(SEQ ID NO: 16)
IRSIGRE;

(SEQ ID NO: 17)
IKSIGRE;
or (SEQ ID NO: 18)
IRSIGRG.
```

In embodiments, the core region of the hC includes one or more heptads described herein, wherein n is 2, 3, 4, 5, 6, 7, 8, 9, 10, or 11.

The present disclosure describes a core region of the hC that includes a peptide of at least 14 residues. In embodiments, the peptide includes 14 residues to 80 residues in length and includes two to 11 heptad repeats. In embodiments, the hC core region includes a peptide comprising 20 to 70 residues, 25 to 60 residues, 28 to 50 residues, 28 to 40 residues, or 28 to 30 residues. The peptides including 14 residues to 80 residues in length are monomers.

The terms "monomeric peptide (MP)" and "monomeric hC (MhC) peptide" are used interchangeably to refer to the monomeric peptides described herein. In embodiments, the exemplary monomeric peptides or monomeric hC peptides described herein include the following amino acid sequences:

```
                                    (SEQ ID NO: 19)
LRSIGKDLRSIGKDLRSIGKDLRSIGKD (SEQ ID NO: 20)
LRSIGKDLRSIGKDLRSIGKDLRSIGKDS;

(SEQ ID NO: 21)
LRSIGKDLRSIGRDLRSIGKDLRSIGRD;

(SEQ ID NO: 22)
IREISRAIREVAQSIRDIAKAIREIGKS;

(SEQ ID NO: 23)
IRDIGRAIRDVGQSIRDLAKGIRDISKG;

(SEQ ID NO: 24)
VKDVARGIRDIGNSIKDLARGIRDIGRG;

(SEQ ID NO: 25)
IRSIGKEIRSIGREIKSIGREIRSIGRG;

(SEQ ID NO: 26)
IRSIGKEIRSIGREIRSIGKEIRSIGRE;
or (SEQ ID NO: 27)
IRSIGKEIRSIGREIRSIGREIRSIGRE.
```

The peptides described herein can be modified to include one or more substitutions, insertions, and/or deletions and maintain the pattern of hwxhxyz (SEQ ID NO: 1), described above. The modification at each position within the heptad repeat or the peptide must maintain the amphipathic alpha-helical structure, stability, and oligomerization state of the peptide.

In embodiments, the peptides described herein include peptides that comprise an amino acid sequence having at least 70%, 75%, 80%, 85%, 90%, 95%, 96%, 97%, 98%, 99%, or 100% sequence identity to (SEQ ID NO: 3)n, (SEQ ID NO: 4)n, (SEQ ID NO: 5)n (SEQ ID NO: 6)n, (SEQ ID NO: 7)n, (SEQ ID NO: 8)n, (SEQ ID NO: 9)n, (SEQ ID NO: 10)n, (SEQ ID NO: 11)n, (SEQ ID NO: 12)n (SEQ ID NO: 13)n, (SEQ ID NO: 14)n, (SEQ ID NO: 15)n, (SEQ ID NO: 16)n, (SEQ ID NO: 17)n, or (SEQ ID NO: 18)n, wherein n is an integer from 2 to 11. In embodiments, the peptides described herein include peptides that comprise an amino acid sequence having at least 70%, 75%, 80%, 85%, 90%, 95%, 96%, 97%, 98%, 99%, or 100% sequence identity to SEQ ID NOs: 19, 20, 21, 22, 23, 24, 25, 26, or 27. Sequence identity refers to the degree of correspondence of two sequences in an alignment, often expressed as a percentage. Differences between two sequences may be determined by methods routinely practiced in the art to determine identity, which are designed to give the greatest match between the sequences tested. Methods to determine sequence identity can be determined by using publicly available computer programs. Computer program methods to determine identity between two sequences include BLASTP. The BLAST family of programs is publicly available from NCBI and other sources.

In embodiments, one or more residues can be added to the N- or C-terminus of the monomer peptides described herein to increase the stability of the peptides in vivo. For example, V (valine), M (methionine), G (glycine), I (isoleucine), D (aspartic acid), or P (proline) or a combination of these residues can be added to the N- or C-terminus of the peptides. Moreover, protective groups can be added to residues to increase the stability of the peptides. Examples of such protective groups include acetyl, acryl, 9-fluorenyl-methoxycarbonyl, tert-butyloxycarbonyl, allyloxycarbonyl, benzyloxycarbonyl, and PEG (polyethyleneglycol), and amide on the C-terminus.

The peptides described herein can be a monomeric hC peptide, but since the monomeric hC peptide is self-assembling, it can self-assemble into a hC that is an oligomer composed of a dimer, trimer, tetramer, pentamer, hexamer, heptamer, octamer, nanomer, or decamer. In embodiments, the monomeric peptide self-assembles into a hexamer, which has six amphipathic alpha-helices. In embodiments, the hC is a hexameric oligomer.

In embodiments, the present disclosure describes a hC that includes one or more residues for conjugating a hapten, such as GnRH. The optimal site on the hC for conjugating to hapten is the y residue in the heptad repeat, but GnRH coupling could also take place at the w, x, and z residues if they contain a reactive side-chain since they are solvent accessible, and GnRH can be covalently attached using any residue that can covalently join GnRH to the hC, including the HhC. In embodiments, the y residue is K, H, C, D, E, R, W, Y, Q, N, or a non-natural amino acid containing reactive groups amenable to covalent coupling. In embodiments, there are two to four y residues on one side of each of the six amphipathic alpha-helices to provide a coupling site. In embodiments, the y residue is lysine (K).

In embodiments, one or more GnRH peptides can be conjugated to the MP during SPPS or after MP has assembled into an oligomer, such as a hexamer, using the y residue. The GnRH conjugated to the hC is conjugate and is referred to as the GnRH-hC conjugate or GnRH-oligomer conjugate. In embodiments, the hC is linked to one to 100, 10 to 90, 20 to 80, 30 to 70, 40 to 60, or 50 GnRH peptides. In embodiments, the hC is HhC, and the conjugate is the GnRH-HhC.

In embodiments, the GnRH peptide can be added during SPPS to the N- and/or C-terminus of the monomeric peptide (prior to self-assembly) to form a GMP. The GMP can then self-assemble into an oligomer, such as a GnRH oligomer or more specifically a GnRH HhC (GnRH hexameric hC or GHhC).

In embodiments, a hMP (hapten attached to a monomeric peptide) can self-assemble into a hhC (hapten attached at the N- or C-terminus of a hapten carrier). When the hapten is GnRH (G), the hMP is GMP, which self-assembles into a GhC oligomer, for example a GHhc (GnRH joined to a hexameric hapten carrier).

The GnRH peptides include GnRH 1 and GnRH 2. The GnRH peptides have different names including Gonadotropin releasing hormone (GnRH or GRH), LHRH (luteinizing hormone releasing hormone), and Gonadotropin-releasing factor (GRF or GnRF).

The GnRH peptide can be found in various vertebrates. Examples of vertebrates include mammals, fish, avians, reptilians, and amphibians. Examples of mammals include primates, rodents, rabbits and hares, canines, equines, porcines, whales, dolphins, bats, odd-toed and even-toed ungulates, and other placentals. Mammals also include monotremes and marsupials. Examples of fish include sharks, rays, bony fish, dogfish, sturgeons, catsharks, and coelacanth. Examples of avians include birds, chickens, and turkeys. Examples of reptiles include snakes. Examples of amphibians include frogs, toads, and caecilians. Thus, vertebrates are good sources of GnRH.

Moreover, the amino acid sequence for GnRH peptides in vertebrates are highly conserved. Their amino acid sequences can be represented by include the following consensus sequence:

$$\text{X}_1\text{HWSX}_2\text{GX}_3\text{X}_4\text{PG,} \hspace{2cm} \text{(SEQ ID NO: 28)}$$

wherein $X_1$ is a polar or charged amino acid; $X_2$ is a polar amino acid; $X_3$ is a hydrophobic or amphipathic amino acid; and $X_4$ is a hydrophobic, amphipathic, charged, or polar amino acid. Amino acids that are charged include R, K, D, or E. Amino acids that are polar include Q, N, H, S, T, Y, or C. Amino acids that are amphipathic include W, Y, or M. Amino acids that are hydrophobic include A, I, L, M, F, V, P, or G. In embodiments, $X_1$ is Q or E. In embodiments, $X_2$ is Y or H. In embodiments, $X_3$ is L or W. In embodiments, $X_4$ is L, Y, R, or Q. In embodiments, $X_1$ is Q or E; $X_2$ is Y or H; $X_3$ is L or W; and $X_4$ is L, Y, R, or Q.

In embodiments, the GnRH peptide is a GnRH 1 peptide comprising the following amino acid sequence: QHWSYGLRPG (SEQ ID NO: 29). In vivo, the first residue of GnRH is pyro-glutamic acid (pE) which is caused by enzyme catalyzed deamidation and subsequent cyclization of the side chain of Q. Vertebrates which are sources of GnRH peptide including the amino acid sequence SEQ ID NO: 29 include primates (including human), rodents, rabbit and hares, placentals, bats, odd-toed ungulates, whales, dolphins, even-toed ungulates, frogs, toads, marsupials, and caecilians.

In embodiments, the GnRH peptide is a GnRH 1 peptide comprising the following amino acid sequence: QHWSHGWLPG (SEQ ID NO: 30). Vertebrates which are sources of GnRH peptide including the amino acid sequence SEQ ID NO: 30 include spiny dogfish, smaller spotted catshark, and coelacanth.

In embodiments, the GnRH peptide is a GnRH 1 peptide comprising the following amino acid sequence: EHWSYGLRPG (SEQ ID NO: 31). Vertebrates which are sources of GnRH peptide including the amino acid sequence SEQ ID NO: 31 include Russian sturgeon and Chinese hamster.

In embodiments, the GnRH peptide is a GnRH 1 peptide comprising the following amino acid sequence: QHWSYGWYPG (SEQ ID NO: 32). Vertebrates which are sources of GnRH peptide including the amino acid sequence SEQ ID NO: 32 include rodents, and snakes, such as the king cobra.

In embodiments, the GnRH peptide is a GnRH 1 peptide comprising the following amino acid sequence: EHWSYGLQPG (SEQ ID NO: 33). Vertebrates which are sources of GnRH peptide including the amino acid sequence SEQ ID NO: 33 include chicken.

In embodiments, the GnRH peptide is a GnRH 2 peptide comprising the following amino acid sequence: QHWSHGWYPG (SEQ ID NO: 34). Vertebrates which are sources of GnRH peptide including the amino acid sequence SEQ ID NO: 34 include primates (including humans), rodents, placentals, birds, turtles, even and odd-toed ungulates, bony fishes, sharks and rays, and chimaeras.

In embodiments, the one or more GnRH peptides that can be attached to the hC can be the same GnRH peptide or different GnRH peptides. As an example, GnRH peptides from different mammalian species can be attached to the same hC. As another example, both GnRH 1 and GnRH 2 can be attached to the same hC. In embodiments, two human isoforms of GnRH, GnRH 1 and GnRH 2, can be attached to the same hC.

In the context of the conjugate or oligomer, the term "attached" or "joined" or "coupled" are used interchangeably to refer to conjugated to the self-assembled oligomer (hC) or added to the monomeric peptide during SPPS prior to self-assembly into an oligomer hC.

One or more residues can be added to the N- or C-terminus of the GnRH peptides described herein. The one or more residues can make the GnRH peptide more stable. For example, the one or more residues increase the in vivo half-life of the GnRH peptide. In embodiments, adding one or more residues to the N-terminus of the GnRH peptide can increase the in vivo half-life of the GnRH peptide more than 5 times to more than 120 times longer than the half-life of a GnRH peptide without one or more added residues at its N- or C-terminus. In embodiments, one or more residues can increase the in vivo half-life of the GnRH peptide more than 5 times, 10 times, 15 times, 20 times, 25 times, 30 times, 35 times, 40 times, 45 times, 50 times, 60 times, 70 times, 80 times, 90 times, 100 times, 110 times, or 120 times longer than the in vivo half-life of a GnRH peptide without an added residue at its N- or C-terminus. In embodiments, residues such as G (glycine), V (valine), M (methionine), or A (alanine), or a combination thereof can be added to the N- or C-terminus of the GnRH peptide for stability. For example, adding G to the N-terminus increases the predicted in vivo half-life of the GnRH peptide from 0.8 hour to greater than 30 hours and adding a V to the N-terminus increases the half-life of the GnRH peptide from 0.8 hour to 100 hours. In embodiments, adding one or more residues, such as G, to the N-terminus of the GnRH peptide increase the half-life of the GnRH peptide by 37.5 times longer, and adding one or more residues, such as V, to the N-terminus of the GnRH increase the half-life of the GnRH peptide to 125 times longer. In embodiments, the GnRH peptide includes amino acid sequence: XQHWSYGLRPG (SEQ ID NO: 35), wherein X is G or V.

In embodiments, the N-terminus of GnRH can also be acetylated for stability.

Other residues also can be added to the N- or C-terminus of the one or more GnRH peptides to help with conjugation to the hC. For example, one or more residues can be added to the N- or C-terminus of the GnRH peptide to reduce the pI (isoelectric point) sufficiently which decreased the electrostatic repulsion with the hC. As an example, residues GEDC (SEQ ID NO: 36) or DGEGC (SEQ ID NO: 37) can be added to the C-terminus as a linker for conjugation and to modify the pI of the GnRH peptide. Moreover, residues GEDC (SEQ ID NO: 36) or DGEGC (SEQ ID NO: 37) can also be added to the N-terminus, in addition to the other residues described above, for improving the stability of the GnRH peptide.

Optionally, other molecules can be conjugated directly to the hC oligomer, such as the HhC, along with the GnRH peptide. Other molecules also can be attached to the GnRH peptide and then conjugated to the hC. Moreover, as mentioned herein, GnRH can be attached to the N- or C-terminus of the hC monomeric peptide during SPPS to form GMP prior to self-assembly into an GhC oligomer, such as a GHhC. One or more other molecules in addition to GnRH can also be attached to the N- or C-terminus of the hC monomeric (MhC) peptide during SPPS prior to self-assembly into a hC oligomer.

Other molecules that can be attached to the hC oligomer or the MP include any agent that can elicit the production of antibodies which are useful for treating, preventing, alleviating the symptoms of prostate cancer, or reducing the risk of developing a disease or disorder in a subject due to elevated levels of testosterone. Examples of other molecules in addition to GnRH include immunomodulators and haptens. Examples of immunomodulators including adjuvanting molecules comprise T-cell epitope peptides, nucleic acids, lipids, lipopeptides, lipoproteins, carbohydrates, and short peptides. Peptides that can be used as haptens, including GnRH, and B-cell epitopes, include synthetically or recombinantly produced or native peptides or proteins comprising natural or non-natural D- or L-amino acids.

T-cell epitopes that can be used for activating a T-cell response (to provide T-cell help to B-cells) can be found in the extracellular proteins of *Clostridium botulinum*, *Clostridium perfringens*, and *Staphylococcus aureus*, and in the extracellular solute binding proteins of *Mycobacterium* and *Clostridium tetani*. T-cell epitopes are also present in *Mycobacterium tuberculosis, Mumps rubulavirus, Plasmodium falciparum*, Human immunodeficiency virus 1, Hepatitis C virus, and Influenza A virus. Examples of such T-cell epitopes include peptides comprising amino acid sequences SEQ ID NOs: 38 and 39 (from the extracellular protein of *Clostridium botulinum*, GenBank: STC78113.1); SEQ ID NO: 40 (from the extracellular protein *Clostridium perfringens*, GenBank: SUY45886.1); SEQ ID NO: 41 (from the extracellular protein *Staphylococcus aureus*, GenBank: SAO03917.1); SEQ ID NOs: 42, 43, 44, 45, and 46 (from the extracellular solute-binding protein of various species of *Mycobacterium*, NCBI Reference Sequence: WP_055398728.1); SEQ ID NOs: 47, 48, and 49 (from the extracellular solute-binding protein *Clostridium tetani*, GenBank: CD150554.1; SEQ ID NO: 50 (from the ESAT-6-like protein EsxB of *Mycobacterium tuberculosis*); SEQ ID NO: 51 (from Alpha-crystallin protein of *Mycobacterium tuberculosis*); SEQ ID NO: 52 (from the mumps rubulavirus protein of Mumps rubulavirus); SEQ ID NO: 53 (from the DNAJ protein of *Plasmodium falciparum*); SEQ ID NO: 54 (from the Gag-Pol polyprotein of Human immunodeficiency virus 1); SEQ ID NO: 55 (from the Genome polyprotein of Hepatitis C virus); SEQ ID NO: 56 (from the Matrix protein 1 of Influenza A virus); and SEQ ID NO: 57 (from Hemagglutinin of Influenza A virus).

Lipids that can be attached to the hC include those that induce an innate immune response through binding to Toll-like receptors (TLR). The lipids can also serve as adjuvanting agents. Example of such lipids include monophosphoryl lipid-A, squalene, lipopolysaccharides (LPS), lipoproteins, or lipopeptides. Carbohydrates that can serve as haptens include glucose, disaccharides, trisaccharides, and larger saccharides, including complex carbohydrates.

Examples of peptides that bind TLR, which can be attached to the hC, include TLR ligands, such as TLR-4 agonistic peptides. These peptides act as an adjuvant peptide. In embodiments, the adjuvant peptide comprises the amino acid sequence APPHALS (SEQ ID NO: 58).

Other molecules can also include haptens, for example B-cell epitopes. B-cell epitopes that can be used as haptens include Kisspeptin peptide, and epitopes derived from the Kisspeptin receptor and GnRH receptor. Also, additional GnRH peptides can be added as other molecules.

When haptens are small peptides, such as GnRH, the entire peptide can be used as a hapten. When the hapten is a protein, a portion is used as a hapten. Portions of a protein to use as a hapten can be determined using in silico prediction algorithms or peptide-based epitope mapping of the entire protein, which are well-known methods. Many T-cell and B-cell epitopes have been identified using these methods.

Haptens which can enhance the immunogenicity of GnRH or enhance the duration or breadth of the immune response of GnRH can be conjugated to the hC along with GnRH. For example, a conjugated peptide that functions to bind a TLR can comprise an adjuvant function and enhance the immunogenicity of GnRH. In embodiments, the GnRH-hC conjugates can include other haptens or peptides in addition to one or more different or the same GnRH peptides.

The present disclosure describes GnRH immunogen which includes GnRH-hC conjugates and GhC oligomers. These conjugates and oligomers can also include other molecules. Peptides used for making the GnRH immunogen include monomeric peptides, the GnRH peptide, other molecules including T-cell epitopes, haptens, and adjuvanting peptides, described herein. They can be chemically synthesized by manual techniques or by automated procedures. As an example, solid phase polypeptide synthesis (SPPS) has been performed since the early 1960's. Over the years, improvements to the early SPPS have been made, and many methods have been automated.

Peptides, in particularly, the longer peptides described herein can be generated by native chemical ligation (NCL). Using NCL, a large peptide (polypeptide) can be formed by ligating (or coupling) two or more smaller peptides. In embodiments, a polypeptide including a monomeric peptide and two or more haptens can be prepared from two or more smaller peptide fragments and assembled together using NCL technology. As an example, a polypeptide including a monomeric peptide and two haptens (one at each N- and C-terminus of the monomeric peptide) can be synthesized from two smaller peptides, which are covalently attached by NCL. Using NCL, a C (cysteine) is added to the N-terminus of one of the two smaller peptides and a thioester functional group is added to the C-terminus of the other of the two smaller peptides and these two peptides are subsequently ligated into the full length polypeptide. In embodiments, residues are added to peptides described herein for ease of synthesis of longer polypeptides.

In embodiments, spacers are added between the monomeric peptide and GnRH peptide or the one or more other haptens. Examples of one or more residues that can be inserted as spacers include G (glycine), D (aspartic acid), S (serine), C (cysteine), or a combination thereof. In embodiments, spacers also include D, GD, or GSG.

The peptides and haptens described herein can also be produced biologically or recombinantly in a heterologous expression system. Any heterologous expression system can be used for producing the peptides described herein. In embodiments, the expression system comprises *E. coli.*, which lacks the machinery for post-translational modification, making it a suitable host for producing the peptides described herein.

Other molecules including GnRH can be attached to the hC using any known method including click chemistry or homo- or heterobifunctional cross-linking reagent or peptide bond formation. In embodiments, haptens can be conjugated to the hC using EDC (1-ethyl-3-(3-dimethylaminopropyl) carbodiimide hydrochloride)/NHS (N-hydroxysuccinimide) or NHS/maleimide cross-linking chemistry, which are routinely used for conjugation reactions. The y residues, for example lysines, are positioned to provide well defined hapten placement and coupling stoichiometry.

Other molecules including GnRH can also be attached to the hC via any suitable linker moiety. Examples of linkers include those that form amide linkages, ester linkages, and disulfide linkages. The linker can be a cleavable linker such as protease cleavable peptide linker, nuclease sensitive nucleic acid linker, lipase sensitive lipid linker, glycosidase sensitive carbohydrate linker, pH sensitive linker, hypoxia sensitive linker, photo-cleavable linker, heat-labile linker, or enzyme cleavable linker. The linker can also be a non-cleavable linker. Any known method can be used to associate a linker with the hC, for example, click chemistry, passive adsorption, multivalent chelation, high affinity non-covalent binding, or covalent bond formation. A hapten can also be attached to the hC without a linker.

Additionally, other molecules including GnRH can be conjugated to the hC through another molecule. For example, GnRH or another B-cell or T-cell epitope, can be first attached to a carrier for displaying an epitope of interest, and then be conjugated to the HhC. Examples of such carrier include protein, peptide, nanoparticle, virus-like particle, or anything that can function as a carrier for displaying GnRH or other epitopes of interest.

Furthermore, the present disclosure describes a GnRH-hC conjugate or GhC oligomer optionally including one or more other molecules, including those described herein. The one or more other molecules include immunomodulators and/or haptens. In embodiments, the one or more other molecules include T-cell epitopes, B-cell epitopes, short peptides for example GnRH peptide, or a combination thereof. In embodiments, the one or more other molecules are linked to the N- and/or C-terminus of one or more of the helices in the core of the hC. In embodiments, the one or more other molecules are linked to the N-terminus of the one or more helices of the core of the hC. In embodiments, one or more molecules are linked to the C-terminus of the one or more helices of the core of the hC.

In embodiments, the T-cell epitopes at the N- and/or C-terminus of one or more of the helices in the core of the hC recruit T helper cells and induce B cells to produce maximum IgG titers for providing a robust immune response, as well as to promote affinity maturation and class switching. Methods for selecting a T-cell epitope peptide are well-known. For example, a T-cell epitope can be selected by experimental methods known in the art, identified from the scientific literature, predicted using bioinformatics tools, designed de novo, or a combination of these methods. In embodiments, the T-cell epitopes at the N-terminus and C-terminus are the same or different. In embodiments, the T-cell epitopes are, for example, CD4+ T-cell epitopes, which are known to enhance the development of memory B cells and plasma cells that produce high affinity antibodies. In embodiments, T-cell epitopes that can be included in the N- and/or C-terminus of the one or more helices of the hC include TCE1 (SEQ ID NOs: 59 or 78), TCE2 (SEQ ID NO: 60), TCE3 (SEQ ID NO: 61), TCE4 (SEQ ID NO: 62), or a combination thereof. In embodiments, the T-cell epitopes also include peptides comprising amino acid sequence SEQ ID NOs: 50, 51, 52, 53, 54, 55, 56, 57, 59, 60, 61, 62 or 78. One or more of these T-cell epitopes can be attached to the hC or GnRH.

One or more T-cell epitopes and/or B-cell epitopes can also be linked to the GnRH peptide prior to conjugating to the hC. Again, these epitopes are used to recruit T helper cells and induce B-cells to produce maximum IgG titers, as well as to promote affinity maturation and class switching.

When a hapten or immunomodulator, such as T-cell and B-cell epitopes, is linked to GnRH for conjugation to the hC or to the N- and/or C-terminus of monomeric peptide, one or more spacers can be inserted between the hapten and GnRH or between the hapten and the monomeric peptide. Spacers are added for immunomodulators, such as T-cell epitopes, for correct processing of the T-cell epitopes to ensure proteolytic trimming that results in a size that fits into the MHC II binding cleft. Examples of such spacers include residues D (aspartic acid), G (glycine), P (proline), S (serine), or a combination thereof. In embodiments, the spacers include one or more of D, GD, PGP, GSG, GPGP (SEQ ID using any kind of linkers. The linkers can be cleavable or uncleavable. Cleavable linkers include protease cleavable peptide linkers, nuclease sensitive nucleic acid linkers, lipase sensitive lipid linkers, glycosidase sensitive carbohydrate linkers, pH sensitive linkers, enzyme cleavable linkers, heat-labile linkers, photo-cleavable linker. Cross-linkers can also be used by activation of a side chain atom or terminal atom for covalent reaction with an intermediary or final molecule atom to form a covalent bond.

The present disclosure describes scaffold peptides including a hC monomeric peptide and one or more haptens and/or immunomodulators, such as one or more T-cell epitopes and/or GnRH, liked to its N- or C-terminus. As described herein, the scaffold peptides can also include one or more spacers, for example, one or more residues for correct processing of T-cell epitopes or stabilizing the hapten and/or the hC monomeric peptide. Table 1 discloses exemplary scaffold peptides.

TABLE 1

| Name of Scaffold Peptide* | Sequence |
|---|---|
| GnRH-Hex-TCE2 | GQHWSYGLRPGGDIRSIGKEIRSIGREIKSIGREIRSIGRGPGPFNNFTVSFWL RVPRVSASHLEQY (SEQ ID NO: 67) |
| TCE3-Hex-TCE4 | GQEAFSHIRIPLPHDIRSIGKEIRSIGREIRSIGKEIRSIGREFQDAYNAAGGHNAVF (SEQ ID NO: 68) |
| GnRH-Hex-GnRH | GQHWSYGLRPGGSGDIRSIGKEIRSIGREIRSIGREIRSIGREGSGQHWSYGLRPG (SEQ ID NO: 69) |

*The amino acid sequence for GnRH is bolded and underlined. The amino acid sequence for Hex is underlined. The amino acid sequence for the T-cell epitopes are bolded.

NO: 63), GPGPG (SEQ ID NO: 64), GPGPGC (SEQ ID NO: 65), or SGPGPG (SEQ ID NO: 66). In embodiments, the spacer for correct processing of the T-cell epitopes include GPGPG (SEQ ID NO: 64).

Haptens or immunomodulators described herein that are small peptides can be linked at the N- and/or C-terminus of one or more helices of the core of the hC. They can be incorporated into the monomeric peptide, such that they are covalently attached to the N- and/or C-terminus of the monomeric peptide using solid phase synthesis or native chemical ligation (NCL). The haptens can be covalently attached to the N- and/or C terminus using homo or hetero-bifunctional cross-linkers or using click chemistry reagents, which are well-known reagents for coupling molecules. In embodiments, the immunomodulators or haptens, for examples the T-cell epitopes and/or B-cell epitopes, are already attached to the N- and/or C-terminus prior to self-assembly into the hC core, such as the HhC core, and the GnRH can be conjugated after the self-assembly into the hC core.

The haptens or immunomodulators at the N- and/or C-terminus can also be linked or conjugated to the hC through either an intermediary functional reagent such as a reactive small molecule or a large molecule. Examples of such small molecule include a catalyst, a stable intermediate, or a salt. Examples of such large molecule include a multiple antigenic peptide, protein, or enzyme.

Further, the conjugation of haptens including GnRH and/or other molecules to the core of the hC can be performed As an example, the GnRH-Hex-TCE2 scaffold peptide includes the GnRH peptide, the hC monomeric peptide (SEQ ID NO: 25), and the T-cell epitope 2 (TCE2) peptide. It also includes one or more stabilizing residues and one or more residues as one or more spacers. For example, a G is added at the N-terminus of the GnRH peptide to stabilize the peptide; GD is inserted as spacers between the GnRH peptide and the monomeric peptide; and PGP is inserted between the monomeric peptide and TCE2. The GnRH peptide and one or more T-cell epitopes are attached to the hC monomeric peptide prior to self-assembly. In embodiments, the hC monomeric peptide (SEQ ID NO: 25) self-assembles into a hexamer to form a scaffold peptide. Accordingly, the scaffold peptide, GnRH-Hex-TCE2, includes a hexameric (Hex) core.

The present disclosure also describes peptide immunogens for conjugating to the hC to form hapten-hC conjugates for the preparation of therapeutics. The peptide immunogens include one or more haptens, for example, a GnRH peptide and optionally one or more immunomodulators, such as a T-cell epitope. As described herein, the peptide immunogens can also include one or more other residues for stabilizing the hapten, such as for stabilizing the GnRH peptide, or for correct processing of T-cell epitopes. Table 2 discloses exemplary immunogens for conjugating to the hC.

TABLE 2

| Name of Peptide Immunogen* | Sequence |
| --- | --- |
| GnRH | QHWSYGLRPGDGEGC (SEQ ID NO: 70) |
| GnRH-TCE1 | QHWSYGLRPGSGPGPGLTAELKIYSVIQAEINKHLGPGPGSFERFEIFPKEGPGPGC (SEQ ID NO: 71) |

*The amino acid sequence for GnRH is bolded and underlined, and the amino acid sequence for the T-cell epitopes are bolded.

Additionally, the present disclosure describes hapten-hC conjugates. Exemplary hapten-hC conjugates include: GnRH-Hex-TCE2+GnRH-TCE1; TCE3-Hex-TCE4+ GnRH; TCE3-Hex-TCE4+GnRH-TCE1; and GnRH-Hex-GnRH+GnRH-TCE1. The "+" indicates that it is a conjugate and that the immunogen is conjugated to the scaffold peptide. As an example, the GnRH-Hex-TCE2+GnRH-TCE1 conjugate includes the immunogen GnRH-TCE1 peptide (the hapten) conjugated to the GnRH-Hex-TCE2 (GHhC) scaffold peptide.

In embodiments, the scaffold peptides (hapten-hC oligomers) described herein can also be immunogens. Examples of such oligomer scaffold peptides include: GnRH-Hex-TCE2; TCE2-Hex-GnRH; GnRH-Hex-GnRH; and GnRH-Hex. These exemplary hapten-hC oligomers can serve as both peptide immunogens and scaffold peptides. Optionally, additional haptens, such as GnRH, can be conjugated to the oligomer core of these scaffold peptides.

The hapten-hC conjugates and the hapten-hC oligomers described herein are used to prepare compositions, such as pharmaceutical compositions. Pharmaceutical compositions including one or more hapten-hC conjugates and one or more hapten-hC oligomers can be used as therapeutics or used to prepare therapeutics or therapeutic compositions. The pharmaceutical compositions described herein are also immunogenic compositions comprising immunomodulators, as they enhance the immunogenicity of haptens, for example, the GnRH peptide. The pharmaceutical compositions described herein are also therapeutic compositions, as they can be used to treat patients in need thereof.

The present disclosure describes compositions including the hC described herein and one or more excipients. In embodiments, the hC is attached to one or more GnRH peptides and/or haptens or modulators (hapten-hC conjugate or GhC oligomer) and optionally to one or more T-cell epitopes at the one or more N- and/or C termini of the amphipathic helices of the core of the hC. In embodiments, the composition is a pharmaceutical composition and the excipient is a pharmaceutically acceptable excipient. In embodiments, the hC is HhC.

The term "excipient" refers to a diluent, adjuvant, or vehicle with which the hC is administered. Examples of adjuvants include complete and incomplete Freund's adjuvant, which are used with animals, particularly research animals. Pharmaceutically acceptable excipients can be sterile liquids, such as water and oils, including those of petroleum, animal, vegetable or synthetic origin, such as peanut oil, soybean oil, mineral oil, sesame oil and the like. Water is a preferred excipient when the pharmaceutical composition is administered intravenously. Saline solutions and aqueous dextrose and glycerol solutions can also be employed as liquid excipients, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Pharmaceutically acceptable adjuvants include those that are based on monophosphoryl lipid-A mixed with an oil, for example, squalene.

The composition or pharmaceutical composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard excipients such as pharmaceutical grades of mannitol, lactose, starch, magnesium stearate, sodium saccharine, cellulose, magnesium carbonate, etc. Such formulation will contain a therapeutically effective amount of the hC, in purified form, together with a suitable amount of excipient to provide the form for proper administration to the subject. The formulation should suit the mode of administration.

The administration of the pharmaceutical compositions described herein may be carried out in any convenient manner, including by aerosol inhalation, injection, ingestion, transfusion, implantation or transplantation. The compositions described herein also can be administered to a subject orally, topically, intranasally, enterally, rectally, buccally, vaginally, sublingually, subcutaneously, intradermally, intratumorally, intranodally, intramedullary, intramuscularly, intravenously, intracranially, intraperitoneally, or a combination thereof. The administration of the pharmaceutical composition can be in any manner that is effective to deliver a therapeutically and/or prophylactically effective amount of the conjugate described herein to the subject in need thereof.

The compositions described herein include immunogenic compositions. In embodiments, the compositions herein are therapeutics. The present disclosure describes a peptide scaffold for producing a GnRH immunogenic therapeutic. The present disclosure also describes a method of preparing a therapeutic which includes designing and preparing a monomeric peptide for the core of the hC described herein, allowing the monomeric peptide to oligomerize, and conjugating one or more GnRH peptides to the oligomerized hC to obtain, for example, a GnRH+hC (GnRH-hC) conjugate. Additionally, the present disclosure describes a method of preparing a therapeutic which includes which includes designing and preparing a monomeric peptide for the core of the hC described herein, covalently attaching a hapten, such as the GnRH peptide, to the monomeric peptide, and allowing the monomeric peptide to oligomerize to obtain a hapten-HC oligomer, such as GhC oligomer. As described above, the monomeric peptide can be synthesized by SPPS which includes providing the prepared monomeric peptide in lyophilized form. Hydration of the lyophilized monomeric peptide allows oligomerization to take place. PBS, which includes salt and buffering capability, can be used to hydrate the lyophilized monomeric peptide. In embodiments, the oligomerized hC is a HhC.

The methods described herein include increasing the immunogenicity of GnRH. The methods include conjugating GnRH to the hC described herein. The method can further include synthesizing a monomeric peptide with one or more other haptens or immunomodulators, for example T-cell or B-cell epitopes at the N- and/or C-terminus of the one or more helices of the core of hC. In embodiments, the monomeric peptide is synthesized with a T-cell and/or B-cell epitope present at the N- and/or C-terminus. The increase in immunogenicity of GnRH is compared with the immunogenicity of GnRH by itself, for example, not linked to or associated with the hC or an excipient. Additionally, the methods described herein also include conjugating one or more other haptens or immunomodulators, in addition to GnRH, to increase the immunogenicity of GnRH. Examples of such haptens and immunomodulators include small molecules, lipids, lipoproteins, and TLR-4 agonists.

In embodiments, the present disclosure describes immunogenic compositions comprising the GnRH-hC conjugate as described above. The GnRH-hC conjugate optionally includes one or more T-cell and/or B-cell epitopes and/or one or more additional haptens or immunomodulators, other than GnRH. In embodiments, the hC is a HhC. The immunogenic composition includes one or more pharmaceutically acceptable excipients. The excipient may be an adjuvant which is used to improve or enhance the immune response to the GnRH-hC conjugate in a therapeutically effective manner. The immunogenic composition can be administered to a subject in need thereof by any route described herein for delivering a GnRH immunogenic therapeutic in an effective amount to a cancer patient, or any subject whose testosterone levels need to be reduced.

The dosage for administering the pharmaceutical and immunogenic compositions described herein to a subject will vary with the precise nature of the condition being treated and the recipient of the treatment. The scaling of dosages for human administration can be performed according to art-accepted practices by a physician depending on various factors.

The pharmaceutical or immunogenic composition described herein can be a formulation. In embodiments, the pharmaceutical or immunogenic composition can be formulated for immediate release or for sustained or slow release. Such formulations can be prepared using well known technology. Sustained release formulations can contain the conjugates described herein conjugate dispersed in an excipient matrix and/or contained within a reservoir surrounded by a rate controlling membrane. Excipients for use within such formulations are biocompatible and/or biodegradable. The formulation provides a relatively constant level of active component release. The amount of conjugate contained within a sustained release formulation depends upon the site of implantation, the rate and expected duration of release, and the nature of the condition to be treated or prevented.

The present disclosure also describes kits with unit doses of conjugates described herein. Such kits may include a container containing the unit dose, an informational package insert with instructions for using the kit to treat or prevent a disease or disorder of interest, and optionally an appliance or device for delivery of the composition.

Additionally, the present disclosure describes a method of enhancing the immunogenicity of a hapten such as GnRH. In embodiments, the method includes obtaining a monomeric peptide described herein, allowing the monomeric peptide to self-assemble into an oligomer (a hC), such as a hexamer, and conjugating the hapten, such as the GnRH peptide, to the oligomer (hexamer hC) to obtain a haptenhC, such as GnRH-HhC. Immunomodulators can also be conjugated to the oligomer. In embodiments, the method also includes synthesizing a monomer peptide (MP) to contain a GnRH (G) peptide on the N- and/or C-terminus, and allowing the GnRH-MP (GMP) to self-assemble into an oligomer, such as a hexamer, to obtain a hapten-hC oligomer, such as the GnRH-HhC oligomer. As described herein, the hapten-hC conjugate or oligomer can include one or more additional haptens or immunomodulators such as GnRH, one or more T-cell epitopes, or B-cell epitopes. As described herein, hapten-hC conjugate or oligomer can further include one or more residues for stabilizing the hapten, one or more residues for proper processing of the T-cell epitopes, and/or one or more spacers inserted between the hapten and the monomeric peptide. The methods described herein can be used to prepare therapeutics or therapeutic compositions, such as a GnRH immunogenic therapeutic composition, for administering to subjects in need thereof to prevent or treat the subject.

The present disclosure also describes the use of the conjugates, oligomers, pharmaceutical compositions, therapeutics, therapeutic compositions, and vaccines described herein to treat subjects in need thereof. Similar to the compositions, the vaccines comprise the conjugates or the oligomers described herein. The present disclosure also describes methods for treatment of subjects in need thereof.

The methods described herein include treating subjects such as humans, veterinary animals (dogs, cats, reptiles, birds, etc.), livestock (horses, cattle, goats, pigs, chickens, etc.), and research animals (monkeys, rats, mice, fish, etc.). Subjects in need of a treatment (in need thereof) are subjects having disease or disorders that need to be treated with a GnRH therapeutic or immunogenic composition that will induce an immune response in the subject that is sufficient or therapeutically effective to treat the subject of the disease or disorder. Thus, a subject in need thereof can be a subject diagnosed or suffering from prostate cancer.

As an example, the antibodies induced by vaccination with the GnRH-hC conjugates described herein can neutralize and prevent GnRH from binding to its receptor and block testosterone production. Blocking testosterone production can inhibit cells, such as prostate tumor cells, that require testosterone from proliferating or metastasizing. In embodiments, the methods described herein can be used to treat a subject diagnosed with prostate cancer.

The treatments include administering an effective amount of the conjugate described herein or the composition including the conjugate described in an effective amount. An "effective amount" is the amount of active agent, for example the conjugate or composition described herein, necessary to result in a desired physiological change in vivo or in vitro. A therapeutically effective amount includes those that provide an effective amount.

An efficacious therapeutic contains components able to induce both innate and adaptive immune responses following immunization. Whereas innate immunity is induced using adjuvants, in embodiments, the therapeutic described herein includes the GnRH-hC conjugate containing the adaptive B- and T-cell epitopes as shown in FIG. 1. After GnRH conjugation, the GnRH-hC conjugate contains minimal extraneous sequences for a more focused and robust immune response against the GnRH B-cell epitopes. In embodiments, for CD4+ T-cell activation, the N- and C-termini of each of the six helices and/or the core of the HhC contain species-specific CD4+ T-cell epitopes required for recruiting T-cell help, producing long-lived plasma cells and high titer/high affinity antibodies, and directing a robust immune memory response. These epitopes are placed at the termini of the HhC, so that they do not interfere with hapten coupling. They are chosen to lack lysine and cysteine residues so that they are not haptenized or uncontrollably cross-linked during the B-cell epitope coupling process. It has been shown that lysine haptenization in T-cell epitopes greatly reduces their activity and function. T-cell epitopes from many different species can be acquired from the IEDB database and are chosen based on positive T- and B-cell assays including MHC ligand binding assays, ability to recruit T-cell help, and induction of B-cell proliferation. The modular nature of the therapeutic technology described herein simplifies transferring therapeutic constructs between species, as it is a simple matter of replacing the T-cell epitopes and modifying the B-cell epitope if a different disease or condition is targeted.

Figure 2:
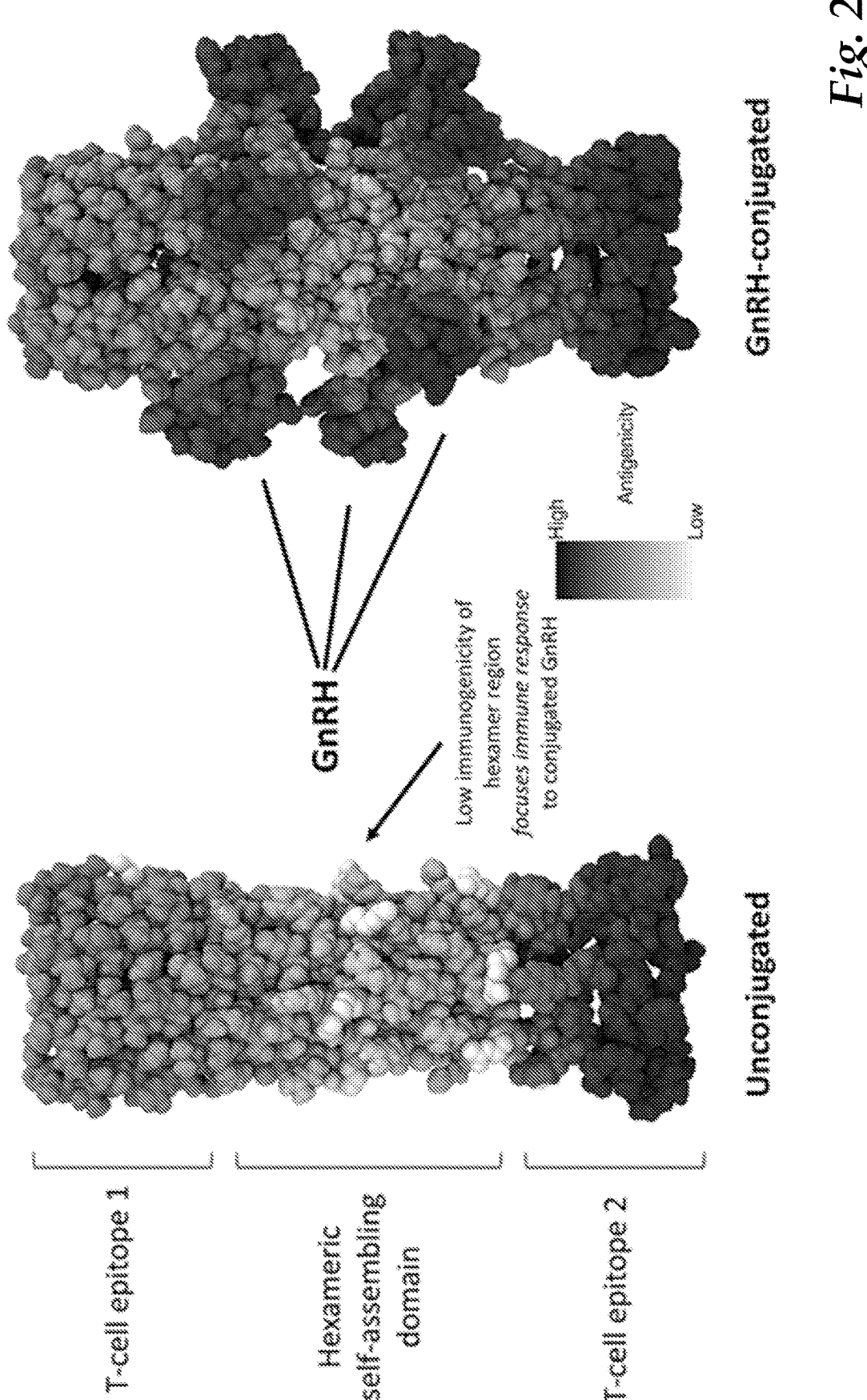
FIG. 2 shows the immunogenicity of the hC (alone) and of the GnRH-hC conjugate. The hC and the GnRH-hC conjugate were first modeled and then subjected to in silico conformational B-cell epitope prediction. The analysis used three web-based servers (BEPro, ElliPro, and DiscoTope 2.0) and one stand-alone Linux program (PTools, which predicts antigenic regions on a protein surface by electrostatic desolvation analysis). Results from all four analyses were normalized, averaged, and the results are shown here.

A distinct advantage of the HhC core region described herein is its reduced immunogenicity (FIG. 2) especially following hapten conjugation, which minimizes the presentation of unproductive immunodominant epitopes. Thus, the combination of presenting multiple GnRH B-cell epitopes with a reduction of non-productive immunodominant epitopes, and the presentation of multiple T-cell epitopes, produces a highly efficacious therapeutic.

The advantages of using a completely synthetic GnRH-hC conjugate therapeutic scaffold or GhC oligomer scaffold are numerous. Modern SPPS routinely produces peptides up to 70-75 residues in length. The HhC described herein will range in size from 55 to 65 residues with the length of the T-cell epitopes defining how much longer than the 28-30 residue core region the HhC will be. The GnRH peptide is 10 residues long and can contain extra amino acids for spacing or imparting unique chemistry, making total synthetic construction of the therapeutic feasible. Producing kilogram quantities of therapeutic peptides in cGMP facilities eliminates costly, time consuming, and resource intensive industrial production and purification of recombinant proteins and there is no need for subsequent viral clearance, endotoxin removal, or testing for the presence of infectious agents. It is usually perceived that peptide synthesis is too costly for large scale therapeutic manufacturing. However, if high nanogram to low µg doses can be used, peptide therapeutics are several-fold more cost effective than GnRH conjugated to recombinant subunit therapeutics.

The terms "residue" and "amino acid" are used interchangeably throughout the disclosure to refer to "amino acid."

As will be understood by one of ordinary skill in the art, each embodiment disclosed herein can comprise, consist essentially of, or consist of its particularly stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. In embodiments, those that do not materially affect the embodiment are those elements, steps, ingredients or components that do not reduce the embodiment's ability in a statistically significant manner to perform a function in vitro or in vivo, such as providing immunity to a disease. In embodiments, the components of the conjugates and oligomers described herein, such as GnRH, hC, or T-cell epitopes, can consist essentially of or can consist of a specific sequence. In embodiments, the therapeutic or therapeutic composition can consist essentially of or can consist of a GnRH-hC conjugate or GhC and an excipient.

In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 15% of the stated value; 10% of the stated value; 5% of the stated value; 4% of the stated value; 3% of the stated value; 2% of the stated value; ±1% of the stated value; or ±any percentage between 1% and 20% of the stated value.

The terms "a," "an," "the" and similar referents used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The following exemplary embodiments and examples illustrate exemplary embodiments provided herein. These examples are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

EXEMPLARY EMBODIMENTS

1. A GnRH conjugate (GnRH-hC) or a GnRH oligomer (GhC) including one or more Gonadotropin releasing hormone (GnRH) peptides covalently attached to a hapten carrier (hC), the hC including an oligomer which includes a monomeric peptide comprising the following amino acid sequence:

$$\text{(hwxhxyz)}n, \quad \text{(SEQ ID NO: 2)}$$

wherein h is a hydrophobic or non-polar residue;

w is a positively charged, negatively charged, polar uncharged, or non-polar aliphatic residue;

x is a negatively charged, positively charged, non-polar aliphatic, or polar uncharged residue;

y is a residue for epitope coupling;

z is a negatively charged, positively charged, polar uncharged, or non-polar aliphatic residue; and n is an integer greater than 1.

2. The GnRH conjugate or GnRH oligomer of embodiment 1, wherein the monomeric peptide includes amino acid sequence SEQ ID NO: 2, wherein h is I, L, V, F, W, Y, M, W, G, or A;

w is G, R, A, N, Q, H, S, D, E, K or T;

x is R, S, N, Q, A, G, T, D, E, K, H, or C;

y is K, H, C, D, E, R, W, Y, Q, N, or a non-natural amino acid or molecule containing reactive groups amenable to covalent coupling;

z is A, D, H, S, E, R, N, Q, K, or G; and n is 2 to 10.

3. The GnRH conjugate or GnRH oligomer of embodiment 1 or 2, wherein the monomeric peptide includes the amino acid sequence SEQ ID NO: 3, 4, 5, 6, 7, 8, 9, 10, 11, 12, 13, 14, 15, 16, 17, or 18.

4. The GnRH conjugate or GnRH oligomer of any one of embodiments 1-3, wherein the monomeric peptide includes the amino acid sequence SEQ ID NO: 19, 20, 21, 22, 23, 24, 25, 26, or 27.

5. The GnRH conjugate or GnRH oligomer of any one of embodiments 1-4, wherein the monomeric peptide further includes residue V, M, G, I, D, P, C, S, C, or a combination thereof at the N-terminus and/or C-terminus.

6. The conjugate or oligomer of any one of embodiments 1-5, wherein the oligomer is a dimer, trimer, tetramer, pentamer, hexamer, heptamer, octamer, nanomer, or decamer.

7. The GnRH conjugate or GnRH oligomer of any one of embodiments 1-6, wherein the oligomer is a hexamer.

8. The GnRH conjugate or GnRH oligomer of any one of embodiments 1-7, wherein the one or more GnRH peptides are obtained from a vertebrate.

9. The conjugate of any one embodiments 1-8, wherein the one or more GnRH peptides are obtained from a mammal.

10. The GnRH conjugate or GnRH oligomer of any one of embodiments 1-9, wherein the one or more GnRH peptides are obtained from a human.

11. The GnRH conjugate or GnRH oligomer of any one of embodiments 1-10, wherein the one or more GnRH peptides include the amino acid sequence:

$$X_1HWSX_2GX_3X_4PG, \quad \text{(SEQ ID NO: 28)}$$

wherein $X_1$ is a polar or charged amino acid;

$X_2$ is a polar amino acid;

$X_3$ is a hydrophobic or amphipathic amino acid; and $X_4$ is a hydrophobic, amphipathic, charged, or polar amino acid.

12. The GnRH conjugate or GnRH oligomer of any one of embodiments 1-11, wherein the one or more GnRH peptides include amino acid sequence SEQ ID NO: 28, wherein $X_1$ is Q or E;

$X_2$ is Y or H;

$X_3$ is L or W; or $X_4$ is L, Y, R, or Q.

13. The GnRH conjugate or GnRH oligomer of any one of embodiments 1-12, wherein the one or more GnRH peptides include amino acid sequence:

QHWSYGLRPG; (SEQ ID NO: 29)

QHWSHGWLPG; (SEQ ID NO: 30)

EHWSYGLRPG; (SEQ ID NO: 31)

QHWSYGWYPG; (SEQ ID NO: 32)

EHWSYGLQPG; (SEQ ID NO: 33)

or

QHWSHGWYPG. (SEQ ID NO: 34)

14. The GnRH conjugate or GnRH oligomer of any one of embodiments 1-13, wherein the one or more GnRH peptides include additional amino acids at the N- and/or C-terminus to stabilize the one or more GnRH peptides and/or for conjugating the one or more GnRH peptides to the hC.

15. The GnRH conjugate or GnRH oligomer of any one of embodiments 1-14, wherein the one or more GnRH peptides include G, V, M, A, or a combination thereof at the N- and/or C-terminus or the N-terminus of the one or more GnRH peptides is acetylated.

16. The GnRH conjugate or GnRH oligomer of any one of embodiments 1-15, wherein the one or more GnRH peptides further include GEDC (SEQ ID NO: 36) or DGEGC (SEQ ID NO: 37) at the N- or C-terminus.

17. The GnRH conjugate or GnRH oligomer of any one of embodiments 1-16, wherein the GnRH conjugate or GnRH oligomer includes two or more GnRH peptides and wherein the GnRH peptides are obtained from different sources and/or include different amino acid sequences selected from SEQ ID NO: 28, 29, 30, 31, 32, 33, or 34.

18. The GnRH conjugate or GnRH oligomer of any one of embodiments 1-17, wherein the one or more GnRH peptides are conjugated to the hC through the y residue on the monomeric peptide.

19. The GnRH conjugate or GnRH oligomer of any one of embodiments 1-18, wherein the GnRH conjugate or GnRH oligomer further includes one or more immunomodulators or additional haptens.

20. The GnRH conjugate or GnRH oligomer of any one of embodiments 1-19, wherein the one or more immunomodulators or additional haptens are covalently fused (incorporated to) the N- and/or C-terminus of the monomeric peptide or covalently attached at one or more N- and/or C-terminus of the oligomer's helices.

21. The GnRH conjugate or GnRH oligomer of any one of embodiments 1-20, wherein the GnRH conjugate or GnRH oligomer includes one or more spacers between the hapten or immunomodulator and the monomeric peptide.

22. The GnRH conjugate or GnRH oligomer of any one of embodiments 1-21, wherein the one or more spacers include G (glycine), D (aspartic acid), S (serine), C (cysteine), or a combination thereof.

23. The GnRH conjugate or GnRH oligomer of any one of embodiments 1-22, wherein the one or more spacers include D, GD, and/or GSG.

24. The GnRH conjugate or GnRH oligomer of any one or embodiments 1-23, wherein the one or more haptens or immunomodulators include GnRH peptide, one or more T-cell epitopes, and/or one or more B-cell epitopes.

25. The GnRH conjugate or GnRH oligomer of any one of embodiments 1-24, wherein the one or more T-cell epitopes include CD4+ T-cell epitopes.

26. The GnRH conjugate or GnRH oligomer of any one of embodiments 1-25, wherein the T-cell epitopes include amino acid sequence SEQ ID NOs: 50, 51, 52, 53, 54, 55, 56, 57, 59, 60, 61, 62, or 78.

27. The GnRH conjugate or GnRH oligomer of embodiment 25 or 26, wherein the GnRH conjugate or GnRH oligomer further include one or more residues for correct processing of the one or more T-cell epitopes.

28. The GnRH conjugate or GnRH oligomer of embodiment 27, wherein the one or more residues include D, G, P, or S, or a combination thereof.

29. The GnRH conjugate or GnRH oligomer of embodiment 27 or 28, wherein the one or more residues include D, GD, PGP, GSG, GPGP (SEQ ID NO: 63), GPGPG (SEQ ID NO: 64), GPGPGC (SEQ ID NO: 65), and SGPGPG (SEQ ID NO: 66).

30. The GnRH conjugate or GnRH oligomer of any one of embodiments 20-29, wherein the one or more immunomodulators or additional haptens enhance the immunogenicity of the one or more GnRH peptides or enhance the duration or breadth of the immune response of the one or more GnRH peptides.

31. The GnRH conjugate or GnRH oligomer of any of any one of embodiments of 20-30, wherein the one or more immunomodulators or additional haptens include a lipid, a peptide, a nucleic acid, or a combination thereof, and wherein the one or more immunomodulators or additional haptens are conjugated to the hC or covalently attached at the one or more N- and/or C-terminus of the oligomer's helices.

32. The GnRh conjugate GnRH oligomer of any one of embodiments 20-31, wherein the one or more immunomodulators or additional haptens include monophosphoryl lipid-A, squalene, lipopolysaccharides, lipoproteins, lipopeptides, APPHALS (SEQ ID NO: 58), Kisspeptin peptide, Kisspeptin receptor, or GnRH receptor.

33. The GnRH conjugate or GnRH oligomer of any one of embodiments 1-32, wherein the GnRH conjugate or GnRH oligomer includes an oligomer scaffold peptide including an amino acid sequence SEQ ID NO: 67, 68, or 69.

34. The GnRH conjugate or GnRH oligomer of any one of embodiments 1-33, wherein the one or more GnRH peptides include an amino acid sequence SEQ ID NO: 70 or wherein the one or more GnRH peptides include GnRH-TCE1 epitope including an amino acid sequence SEQ ID NO: 71.

35. A composition including the GnRH conjugate or GnRH oligomer of any one of embodiments 1-34 and an excipient.

36. The composition of embodiment 35, wherein the composition is a pharmaceutical composition and the excipient is a pharmaceutically acceptable excipient.

37. A method of treating a subject having a disease wherein the method includes administering to the subject in need thereof, an effective amount of the conjugate of any one of embodiments 1-34 or the composition of embodiment 36, wherein the hapten induces an immune response to treat the subject.

38. The method of embodiment 37, wherein the subject is a mammal.

39. The method of embodiment 37 or 38, wherein the subject is a human.

40. The method of any one of embodiments 37-39, wherein the disease is prostate cancer.

41. A method of enhancing the immunogenicity of a GnRH peptide, wherein the method includes:

obtaining a monomeric peptide of any one of embodiments 1-34;

allowing the monomeric peptide to self-assemble into a hC; and conjugating the GnRH peptide of any one of embodiments 1-34 to the hC to obtain a GnRH-hC conjugate.

42. The method of embodiment 41, wherein the GnRH-hC conjugate is a GnRH hexamer (GnRH-HhC) conjugate.

43. A method of enhancing the immunogenicity of a GnRH peptide, wherein the method includes:

synthesizing a GnRH monomeric peptide (GMP), wherein the GMP includes a monomeric peptide of any one of embodiments 1-34 and a GnRH peptide of any one of embodiments 1-34; and allowing the GMP to self-assemble into a GnRH-hC oligomer (GhC).

44. The method of embodiment 42, wherein the GnRH oligomer is a GnRH hexameric oligomer (GHhC).

45. A method of preparing a GnRH therapeutic, wherein the method includes obtaining a monomeric peptide of any one of embodiments 1-34;

allowing the monomeric peptide to self-assemble into a hC; and conjugating the GnRH peptide of any one of embodiments 1-34 to the hC to obtain a GnRH-hC conjugate.

46. The method of embodiment 45, wherein the GnRH-hC conjugate is a GnRH-HhC conjugate.

47. A method of preparing a GnRH therapeutic, wherein the method includes:

synthesizing a GnRH monomeric peptide (GMP), wherein the GMP includes a monomeric peptide of any one of embodiments 1-34 and a GnRH peptide of any one of embodiments 1-34; and allowing the GMP to self-assemble into a GnRH-hC oligomer (GhC), thereby obtaining a GnRH therapeutic.

48. The method of embodiment 42, wherein the GnRH-hC oligomer is a GnRH hexameric oligomer (GHhC).

49. A peptide including a GnRH peptide of any one of embodiments 1-34 and a monomeric peptide of any one of embodiments 1-34.

50. The peptide of embodiment 49, wherein the peptide includes amino acid sequence SEQ ID NO: 67.

51. A peptide immunogen including amino acid SEQ ID NO: 70 or SEQ ID NO: 71.

52. A monomeric peptide including heptads including amino acid sequence SEQ ID NO: 15, 16, 17, or 18.

53. A monomeric peptide including amino acid sequence SEQ ID NO: 25, 26, or 27.

EXAMPLES

Example 1. Constructing a GnRH Therapeutic

There are up to 24 coupling sites on each hexameric carrier for hapten conjugation (FIG. 1), but due to steric hindrance, it is unlikely that conjugation will occur on all sites. It has been previously shown that saturating the carrier with haptens does not always produce the most robust immune response and there is a trade-off between coupling density, epitope spatial/steric availability for correct B-cell epitope presentation, and antibody titer. Therefore, three separate hexamer conjugation reactions were performed to obtain conjugates with different epitope loading levels. For example, one reaction was performed with 3-5 molar equivalents of GnRH so that only 3 or 4 peptides are conjugated, another reaction contains 8 to 10 molar equivalents to form a conjugate with 6-10 peptides, and the third reaction was performed using 25-50 molar equivalents to couple as many epitopes as possible (saturating conditions). FIG. 1 illustrates the GnRH conjugation procedure. GnRH was designed so the N-terminal residue is acetylated to protect the N-terminal amine from derivatization with cross-linkers. The C-terminus included added residues (GEDC) to modulate the pI, because native GnRH has a pI of 8.3 and the pI of the hexameric carrier is 10.1, so the coupling efficiency would be increased by imparting a net negative charge on GnRH. The pI of QHWSYGLRPGGEDC (SEQ ID NO: 72) is 5.3. A C-terminal Cys residue was added for specific covalent attachment via the cysteinyl sulfhydryl group. A Trp residue was present in native GnRH for fluorescence-based peptide quantitation following coupling to determine reaction efficiency.

Tryptophan fluorescence, gel filtration chromatography, native PAGE, and SELDI-TOF (a MALDI-like MS instrument ideally suited for determining the molecular weight of protein-peptide conjugates) are methods used to quantify peptide epitope coupling efficiency. It is relatively straightforward to calculate the number of GnRH peptides conjugated to the hexameric carrier and to BSA (GnRH-BSA was used as a coating reagent in ELISA assays). KLH was used as a positive immunization control because it is an antigenic "gold-standard" hapten carrier. However, it is so large it may only be possible to confirm successful conjugation without calculating the exact number of peptides conjugated.

Example 2. Characterizing GnRH-hC Conjugate Constructs

Adjuvants: To enhance adaptive B- and T-cell responses, regulate the extent of protective immunity, and maximize GnRH-specific antibody responses, adjuvants were used for all immunizations. The best adjuvants directly stimulate dendritic cell maturation and the most effective way to guide this is through TLR-mediated activation. Synthetic TLR4-based adjuvants are some of the most effective, so at least two of these were tested. Monophosphoryl Lipid A (MPL) is a potent TLR4 agonist that can function as the primary adjuvant. MPL is emulsified with squalene (Sq) to form MPL-Sq. Emulsions efficiently prime CD4+ T-cells, which are important for inducing both memory and long-lived GnRH antibody responses. The adjuvants E6020 and GLA, which are approved for use in humans, were also tested. All adjuvants can assist with CD4+ induced GnRH-hC conjugate uptake into dendritic cells and induce the GnRH-hC conjugate specific Th1 CD4+ T cells for binding T-cell epitopes. To assess adjuvant function, both CD4+ T cell and IgG isotype class switching was quantified in immunized mouse sera. Another important benefit of adjuvants is the high likelihood of antigen dose-sparing which is something that will also be tested. Dose-sparing can decrease the amount of GnRH-hC conjugate per immunization and increase the number of doses that can be obtained from a synthetic peptide batch and is a key determinant in reducing synthetic GnRH-hC conjugate manufacturing costs.

For each GnRH-hC conjugate, at least three sets of experiments were performed. Mice received a prime-boost immunization (IM), and B- and T-cell function was measured at several times post immunization. Three dose levels of the GnRH-hC conjugates were compared to determine at which level maximum anti-GnRH IgG titers were obtained. The hexamer is maximally loaded with GnRH and formulated with MPL-Sq adjuvant prior to immunization. Three dose levels (e.g. 0.1, 1, and 10 µg GnRH-hC) were tested and optimized depending on the anti-GnRH IgG titers. This experiment also tests anti-GnRH IgG specificity by measuring IgG response to the hC alone, GnRH alone, and the GnRH+hC (unconjugated but combined).

Mouse immunizations with GnRH-hC Conjugate: Inbred mice (10/grp) received a prime/boost immunization with adjuvanted GnRH-hC conjugate or control (GnRH-KLH conjugate). The first set of studies provided the optimal GnRH-hC conjugate dose and measured anti-GnRH IgG titer at each dose level. Sera were collected 14 days after both the prime and boost (d35) immunizations and antibody mid-point titers are measured. Mouse blood was used for performing B- and T-cell assays.

B-cell function: Standard ELISA was used to measure therapeutic efficacy by GnRH-specific antibody titer in the collected mouse sera. ELISA plates were coated with GnRH-BSA conjugate and 8 sequential 10-fold dilutions (from $1:10^3$ to $1:10^{10}$) of sera in blocking buffer were made and added to the ELISA plate wells. An HRP-labeled anti-mouse secondary antibody was added and the plates developed with a colorimetric substrate and measured in an ELISA plate reader. Data were plotted, curve fitted, and statistically analyzed using Prism Graph Pad software for calculating mid- and end-point titers.

T-cell function: T-cell epitope and adjuvant functions were measured by well-established T-cell ELISA assays. Commercially available coating reagents and primary/secondary antibodies were purchased and used according to the manufacturer's protocols. IFN-$\gamma$, IL-2, IL-4, and TNF-$\alpha$ were quantified in mouse sera as read outs of T-cell function in GnRH-hC conjugate immunized mice. These targets can be expanded to include other markers of T-cell function including IL-5, IL-8, IL-10, IL-12p70, and IL-13. The GnRH-hC conjugate induced T-cell dependent isotype class and subclass switching are assayed by ELISA using reagents specific for total IgG, IgG1, IgG2a, IgG2b, IgG3, IgM, and IgA.

GnRH-hC Conjugate safety: Initial assessments of safety were performed in a non-GLP setting to ensure mice have no adverse reactions to therapeutic components (GnRH-hC, adjuvants). A more precise and detailed safety study were performed later in a GLP study, but this initial evaluation provided some important read-outs to guide therapeutic dose, adjuvant dose, and immunization scheduling. Potential local and systemic toxicities were evaluated by observing injection site reactions and signs of inflammation as well as mouse behavior (e.g. signs of lethargy). If toxicity was observed, different adjuvant and/or T-cell epitopes were evaluated.

Example 3. Preparation of GnRH-hC Conjugates and GHhC for Use as Therapeutics To prepare hapten-hC conjugates, peptide immunogens were covalently coupled to a hexamer scaffold peptide after reduction of the cysteinyl sulfhydryl group with (tris(2-carboxyethyl)phosphine), and then incubating with the oligomer scaffolds that were first activated with a heterobifunctional covalent cross-linker. The peptide immunogens include the GnRH peptide and the GnRH-TCE1 peptide. The hexamer scaffold peptides include GnRH-Hex-TCE2, TCE3-Hex-TCE4, and GnRH-Hex-GnRH. Their sequences are provided in Tables 1 and 2. The following four GnRH constructs (four GnRH-hC conjugates) were prepared from the peptide immunogens and hexamer scaffold peptides of Tables 1 and 2 for use as therapeutics.
1. GnRH-Hex-TCE2+GnRH-TCE1
2. TCE3-Hex-TCE4+GnRH
3. TCE3-Hex-TCE4+GnRH-TCE1
4. GnRH-Hex-GnRH+GnRH-TCE1 GnRH construct 5 (GHhC) is a scaffold peptide obtained by attaching the GnRH peptide and the TCE2 to the N- and C-terminus of the monomeric peptide (see Table 1) during SPPS and then allowing the monomeric peptide to assemble.
5. GnRH-Hex-TCE2

Since keyhole limpet hemocyanin (KLH) is routinely used as a carrier protein for haptens in the production of antibodies, KLH was selected for use a control. The following two constructs (conjugates) were prepared for use as controls.
6. KLH+GnRH
7. KLH+GnRH-TCE1

Constructs 1-7 (1 and 10 ug) were adjuvanted with a monophosphoryl lipid-A/squalene-based adjuvant and injected into BALB/cJ mice. Each construct is injected into 5 mice (n=5 per construct). After 14, 28, and 42 days, mouse sera were obtained to measure anti-GnRH IgG endpoint titers by ELISA using dilutions from $10^{-3}$ to $10^{-9}$ (sequential 10-fold dilutions). To confirm therapeutic function, testosterone was measured in an aliquot of sera from 3 groups: two of the constructs with highest antibody titers (TCE3-Hex-TCE4+GnRH and GnRH-Hex-GnRH+GnRH-TCE1 (construct 4)), a positive KLH control (KLH+GnRH), and a PBS negative control (PBS+adjuvant). Testosterone was extracted from the sera, derivatized, and separated and quantified by LC-MS/MS.

FIG. 3 shows antibody endpoint titers in mice immunized with 5 different GnRH therapeutics (constructs 1-5), three positive controls (constructs 6 and 7 and ReproBloc, which is a GnRH subunit vaccine used in veterinary applications), and one negative control (PBS+adjuvant) at 14, 28, and 42 days post-prime immunization. The solid line in the group of dots is the geometric mean and the error bars are the geometric standard deviation. Two doses were chosen for this study: 1 and 10 ug. IgG titers reached maximum levels 42 days following prime immunization. In 3 out of the 5 GnRH constructs, maximum titers were reached at 1 ug. One construct had equal antibody titers at both 1 and 10 ug (TCE3-Hex-TCE4+GnRH (construct 2)). This same construct induced titers at almost equal levels between d28 and d42 (not a significant increase at d42).

Figure 4:
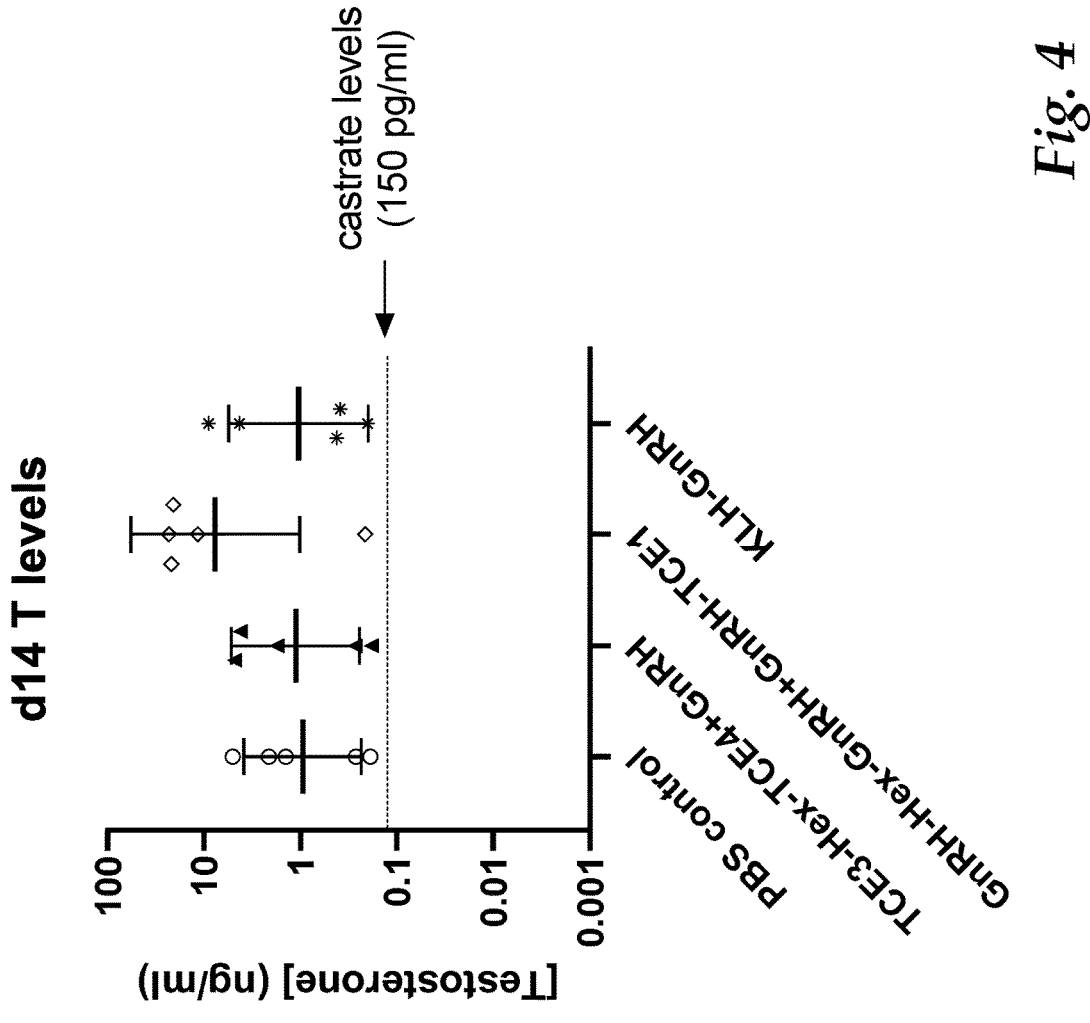
FIG. 4 shows mouse anti-GnRH IgG titers and testosterone (T) levels at d14 induced by exemplary GnRH-HhC conjugates and a GHhC oligomer compared to controls.
Figure 4:
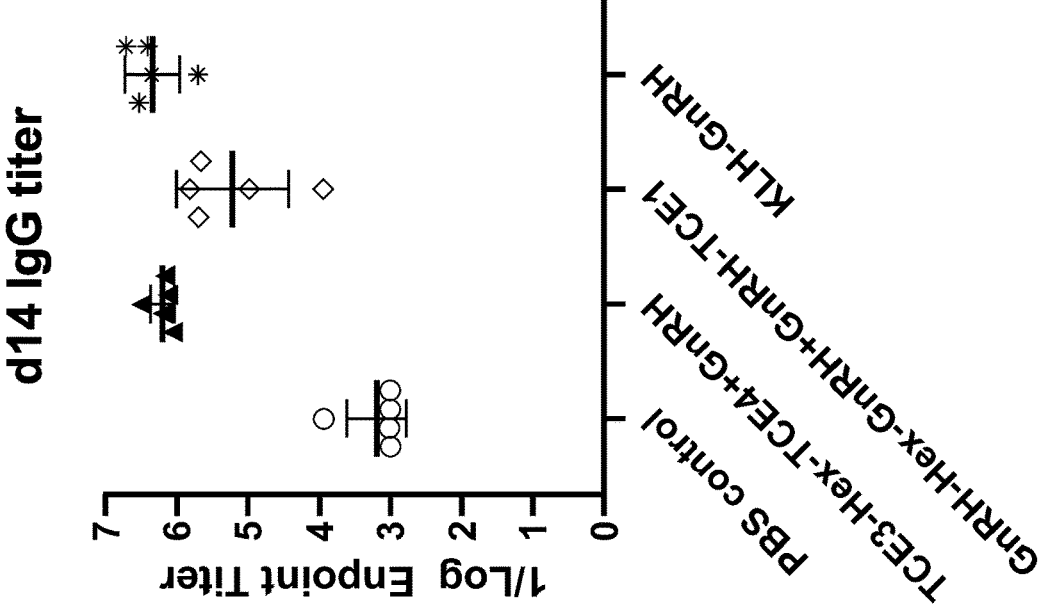
Figure 5:
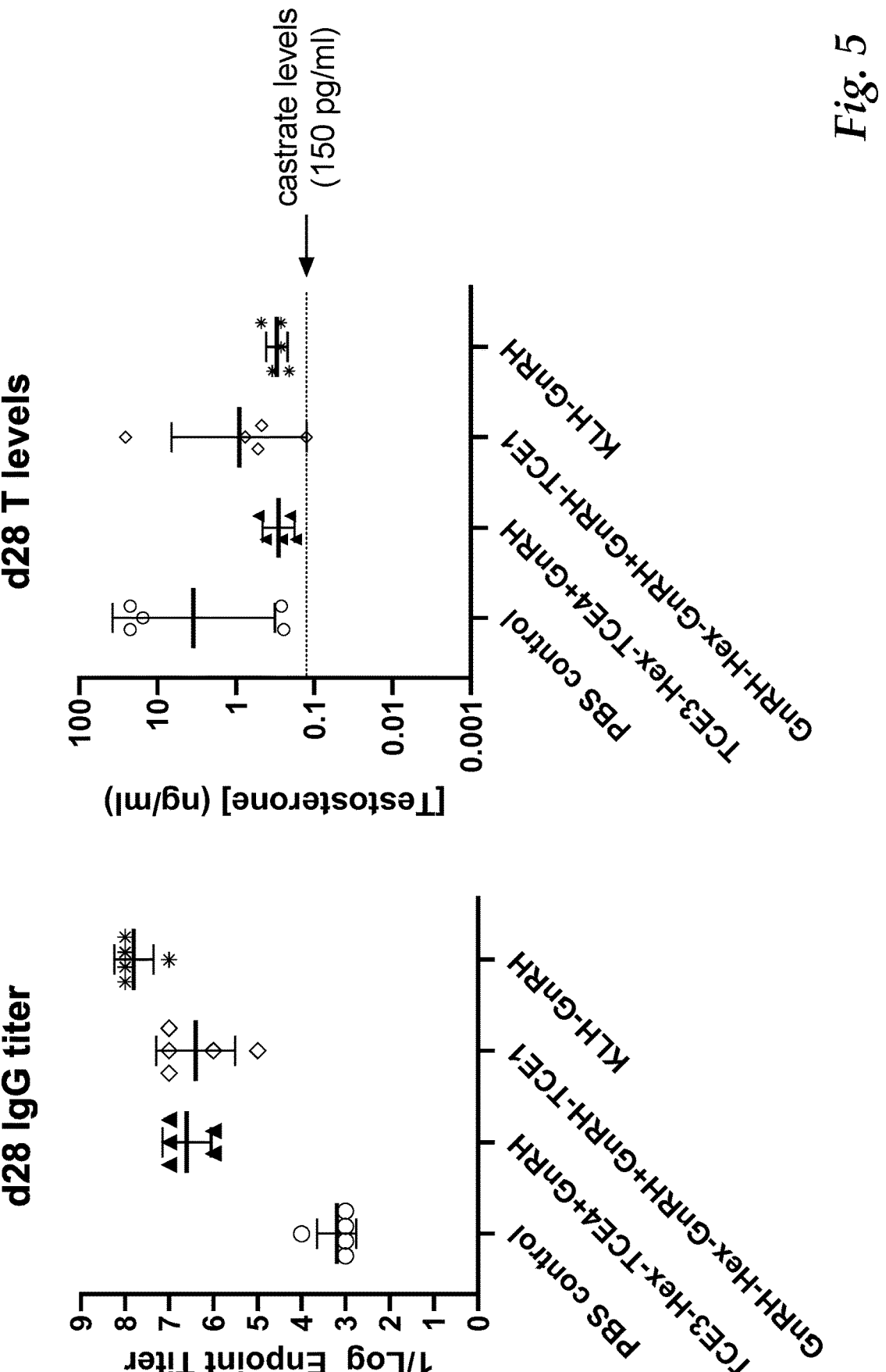
FIG. 5 shows mouse anti-GnRH IgG titers and T levels at d28 induced by exemplary GnRH-HhC conjugates and a GHhC oligomer compared to controls.
Figure 6:
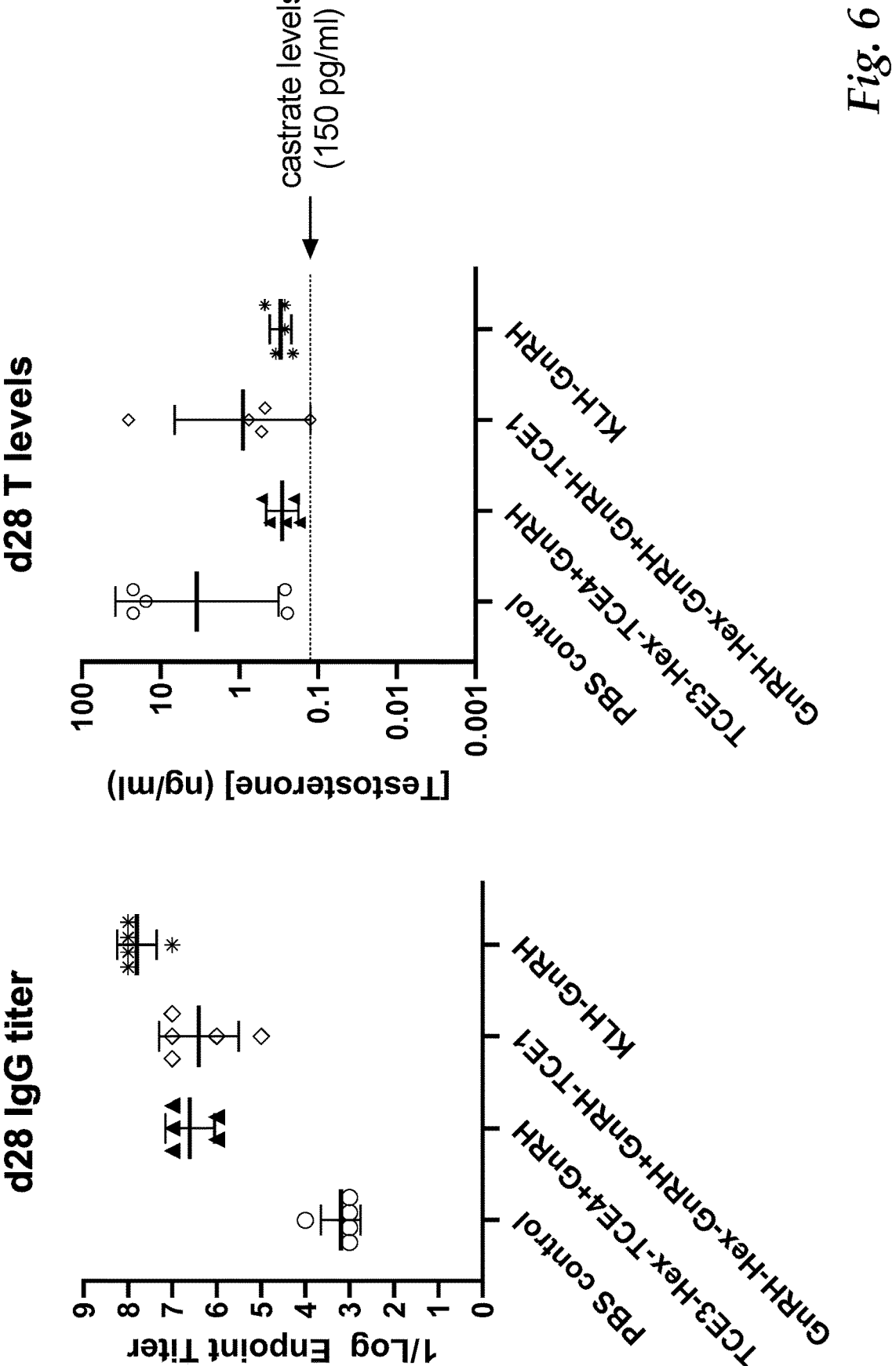
FIG. 6 shows mouse anti-GnRH IgG titers and T levels at d42 induced by exemplary GnRH-HhC conjugates and a GHhC oligomer compared to controls.

Construct 2 ((TCE3-Hex-TCE4+GnRH) and construct 4 (GnRH-Hex-GnRH+GnRH-TCE1) and construct 5 were chosen to confirm therapeutic function by measuring testosterone levels because they had the highest titers or induced high titers sooner (FIG. 3). Testosterone (T) levels in mice immunized with this construct 2 or construct 4 as well as one positive control (KLH+GnRH (construct 6), and one negative control (PBS control), were analyzed and quantified using LC-MS/MS. FIGS. 4-6 show testosterone levels in each mouse as well as the corresponding antibody titer data (shown in FIG. 3). The IgG titer and T level for each mouse is depicted by an individual shape. T levels at d14, d28, and d42 were measured to determine at which time point castrate levels of T were observed. A castrate T level is shown by the dotted line. FIG. 6 shows by d42, anti-GnRH IgG titers for both constructs induced castrate levels of T and resulted in antibody titers and T levels similar to the KLH+GnRH positive control.

FIGS. 4-6 confirms that GnRH-HhC conjugates, for example TCE3-Hex-TCE4+GnRH and GnRH-Hex-GnRH+GnRH_TCE1 are at about the same as KLH+GnRH (positive control) at inducing IgG titers and castrate levels of T and are useful as therapeutics for treating diseases such as prostate cancer.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

REFERENCES

Betakova, T., D. Svetlikova and M. Gocnik, 2013 Overview of measles and mumps vaccine: origin, present, and future of vaccine production. Acta Virol 57: 91-96.

Bill, R. M., 2015 Recombinant protein subunit vaccine synthesis in microbes: a role for yeast? J Pharm Pharmacol 67: 319-328.

Buckland, B. C., 2015 The development and manufacture of influenza vaccines. Hum Vaccin Immunother 11: 1357-1360.

Butler, M., and M. Spearman, 2014 The choice of mammalian cell host and possibilities for glycosylation engineering. Curr Opin Biotechnol 30: 107-112.

Chou, M. L., A. Bailey, T. Avory, J. Tanimoto and T. Burnouf, 2015 Removal of transmissible spongiform encephalopathy prion from large volumes of cell culture media supplemented with fetal bovine serum by using hollow fiber anion-exchange membrane chromatography. PLoS One 10: e0122300.

Ciabattini, A., E. Pettini, F. Fiorino, S. Lucchesi, G. Pastore et al., 2018 Heterologous Prime-Boost Combinations Highlight the Crucial Role of Adjuvant in Priming the Immune System. Front Immunol 9: 380.

Clark, T. G., and D. Cassidy-Hanley, 2005 Recombinant subunit vaccines: potentials and constraints. Dev Biol (Basel) 121: 153-163.

Corradin, G., N. Cespedes, A. Verdini, A. V. Kajava, M. Arevalo-Herrera et al., 2012 Malaria vaccine development using synthetic peptides as a technical platform. Adv Immunol 114: 107-149.

Corradin, G., A. V. Kajava and A. Verdini, 2010 Long synthetic peptides for the production of vaccines and drugs: a technological platform coming of age. Sci Transl Med 2: 50rv53.

Del Giudice, G., R. Rappuoli and A. M. Didierlaurent, 2018 Correlates of adjuvanticity: A review on adjuvants in licensed vaccines. Semin Immunol.

Evans, J. T., C. W. Cluff, D. A. Johnson, M. J. Lacy, D. H. Persing et al., 2003 Enhancement of antigen-specific immunity via the TLR4 ligands MPL adjuvant and Ribi.529. Expert Rev Vaccines 2: 219-229.

Fiorucci, S., and M. Zacharias, 2010 Prediction of protein-protein interaction sites using electrostatic desolvation profiles. Biophys J 98: 1921-1930.

Fiorucci, S., and M. Zacharias, 2014 Computational antigenic epitope prediction by calculating electrostatic desolvation penalties of protein surfaces. Methods Mol Biol 1184: 365-374.

Genzel, Y., 2015 Designing cell lines for viral vaccine production: Where do we stand?Biotechnol J 10: 728-740.

Grein, T. A., R. Michalsky and P. Czermak, 2014 Virus separation using membranes. Methods Mol Biol 1104: 459-491.

Haste Andersen, P., M. Nielsen and O. Lund, 2006 Prediction of residues in discontinuous B-cell epitopes using protein 3D structures. Protein Sci 15: 2558-2567.

Hermanson, G. T., 2013a Chapter 2—Functional Targets for Bioconjugation, pp. 127-228 in Bioconjugate Techniques (Third Edition), edited by G. T. Hermanson. Academic Press, Boston.

Hermanson, G. T., 2013b Chapter 6—Heterobifunctional Crosslinkers, pp. 299-339 in Bioconjugate Techniques (Third Edition), edited by G. T. Hermanson. Academic Press, Boston.

Hu, Y. C., 2005 Baculovirus as a highly efficient expression vector in insect and mammalian cells. Acta Pharmacol Sin 26: 405-416.

Hu, Y. C., K. Yao and T. Y. Wu, 2008 Baculovirus as an expression and/or delivery vehicle for vaccine antigens. Expert Rev Vaccines 7: 363-371.

Jespersen, M. C., B. Peters, M. Nielsen and P. Marcatili, 2017 BepiPred-2.0: improving sequence-based B-cell epitope prediction using conformational epitopes. Nucleic Acids Res 45: W24-W29.

Josefsberg, J. O., and B. Buckland, 2012 Vaccine process technology. Biotechnol Bioeng 109: 1443-1460.

Kawakami, K., and R. K. Puri, 2004 Regulatory expectations during product development for tumour vaccines. Dev Biol (Basel) 116: 53-59; discussion 69-76.

Khan, A., S. Datta, S. C. Das, T. Ramamurthy, J. Khanam et al., 2003 Shiga toxin producing Escherichia coli infection: current progress & future challenges. Indian J Med Res 118: 1-24.

Kim, H. J., and H. J. Kim, 2017 Yeast as an expression system for producing virus-like particles: what factors do we need to consider? Lett Appl Microbiol 64: 111-123.

Kost, T. A., and C. W. Kemp, 2016 Fundamentals of Baculovirus Expression and Applications. Adv Exp Med Biol 896: 187-197.

Legastelois, I., S. Buffin, I. Peubez, C. Mignon, R. Sodoyer et al., 2017 Non-conventional expression systems for the production of vaccine proteins and immunotherapeutic molecules. Hum Vaccin Immunother 13: 947-961.

Miller, K. D., R. Roque and C. H. Clegg, 2014 Novel Anti-Nicotine Vaccine Using a Trimeric Coiled-Coil Hapten Carrier. PLoS One 9: el 14366.

Nielsen, J., 2013 Production of biopharmaceutical proteins by yeast: advances through metabolic engineering. Bioengineered 4: 207-211.

Olugbile, S., C. Habel, C. Servis, F. Spertini, A. Verdini et al., 2010 Malaria vaccines—The long synthetic peptide approach: Technical and conceptual advancements. Curr Opin Mol Ther 12: 64-76.

Perez, S. A., E. von Hofe, N. L. Kallinteris, A. D. Gritzapis, G. E. Peoples et al., 2010 A new era in anticancer peptide vaccines. Cancer 116: 2071-2080.

Persing, D. H., R. N. Coler, M. J. Lacy, D. A. Johnson, J. R. Baldridge et al., 2002 Taking toll: lipid A mimetics as adjuvants and immunomodulators. Trends Microbiol 10: S32-37.

Pfaar, O., D. Cazan, L. Klimek, D. Larenas-Linnemann and M. A. Calderon, 2012 Adjuvants for immunotherapy. Curr Opin Allergy Clin Immunol 12: 648-657.

Pietersz, G. A., D. S. Pouniotis and V. Apostolopoulos, 2006 Design of peptide-based vaccines for cancer. Curr Med Chem 13: 1591-1607.

Ponomarenko, J., H. H. Bui, W. Li, N. Fusseder, P. E. Bourne et al., 2008 ElliPro: a new structure-based tool for the prediction of antibody epitopes. BMC Bioinformatics 9: 514.

Roohvand, F., M. Shokri, M. Abdollahpour-Alitappeh and P. Ehsani, 2017 Biomedical applications of yeast—a patent view, part one: yeasts as workhorses for the production of therapeutics and vaccines. Expert Opin Ther Pat 27: 929-951.

Rowland, S. S., R. L. Mayner and L. Barker, 2005 Advancing TB vaccines to Phase I clinical trials in the US: regulatory/manufacturing/licensing issues. Tuberculosis (Edinb) 85: 39-46.

Safdar, A., and M. M. Cox, 2007 Baculovirus-expressed influenza vaccine. A novel technology for safe and expeditious vaccine production for human use. Expert Opin Investig Drugs 16: 927-934.

Sari, D., K. Gupta, D. B. Thimiri Govinda Raj, A. Aubert, P. Drncova et al., 2016 The MultiBac Baculovirus/Insect Cell Expression Vector System for Producing Complex Protein Biologics. Adv Exp Med Biol 896: 199-215.

Seydoux, E., H. Liang, N. Dubois Cauwelaert, M. Archer, N. D. Rintala et al., 2018 Effective Combination Adjuvants Engage Both TLR and Inflammasome Pathways To Promote Potent Adaptive Immune Responses. J Immunol 201: 98-112.

Singh, M., and I. Srivastava, 2003 Advances in vaccine adjuvants for infectious diseases. Curr HIV Res 1: 309-320.

Smith, L. A., M. J. Jensen, V. A. Montgomery, D. R. Brown, S. A. Ahmed et al., 2004 Roads from vaccines to therapies. Mov Disord 19 Suppl 8: S48-52.

Tapia, F., I. Jordan, Y. Genzel and U. Reichl, 2017 Efficient and stable production of Modified Vaccinia Ankara virus in two-stage semi-continuous and in continuous stirred tank cultivation systems. PLoS One 12: e0182553.

Thomson, A. R., C. W. Wood, A. J. Burton, G. J. Bartlett, R. B. Sessions et al., 2014 Computational design of water-soluble alpha-helical barrels. Science 346: 485-488.

van Oers, M. M., 2006 Vaccines for viral and parasitic diseases produced with baculovirus vectors. Adv Virus Res 68: 193-253.

Vlak, J. M., and R. J. Keus, 1990 Baculovirus expression vector system for production of viral vaccines. Adv Biotechnol Processes 14: 91-128.

Warnock, J. N., and M. Al-Rubeai, 2006 Bioreactor systems for the production of biopharmaceuticals from animal cells. Biotechnol Appl Biochem 45: 1-12.

Wood, C. W., J. W. Heal, A. R. Thomson, G. J. Bartlett, A. A. Ibarra et al., 2017 ISAMBARD: an open-source computational environment for biomolecular analysis, modelling and design. Bioinformatics 33: 3043-3050.

Wood, C. W., and D. N. Woolfson, 2018 CCBuilder 2.0: Powerful and accessible coiled-coil modeling. Protein Sci 27: 103-111.

Wu, Y., and J. H. Collier, 2017 alpha-Helical coiled-coil peptide materials for biomedical applications. Wiley Interdiscip Rev Nanomed Nanobiotechnol 9.

Yamada, A., T. Sasada, M. Noguchi and K. Itoh, 2013 Next-generation peptide vaccines for advanced cancer. Cancer Sci 104: 15-21.

Zaccai, N. R., B. Chi, A. R. Thomson, A. L. Boyle, G. J. Bartlett et al., 2011 A de novo peptide hexamer with a mutable channel. Nat Chem Biol 7: 935-941.

Geysen et al., J. Immun. Meth. 102:259-274 (1987)

Miranda et al., Proc. Natl. Acad. Sci. USA 96:1181-86 (1999)

Merrifield, J. Am. Chem. Soc. 85:2149-2154 (1963))

Altschul, S. F. et al., J. Mol. Biol. 215: 403-410 (1990)

Pearson and Lipman, Proc. Natl. Acad. Sci. USA 85; 2444-2448 (1988)

BLAST Manual, Altschul, S., et al., NCBI NLM NIH Bethesda, Md.)

The invention claimed is:

1. A scaffold peptide including one or more Gonadotropin releasing hormone (GnRH) peptides covalently attached to a monomeric peptide,
wherein the monomeric peptide comprises amino acid sequence SEQ ID NO: 3, 4, 5, 6, 7, 8, 9, 10, 11, 12, 13, 15, 16, 17, or 18; or
wherein the monomeric peptide comprises the amino acid sequence SEQ ID NO: 19, 20, 21, 22, 23, 24, 25, 26 or 27.

2. The scaffold peptide of claim 1, wherein the one or more GnRH peptides comprise the amino acid sequence:

$$X_1HWSX_2GX_3X_4PG,$$ (SEQ ID NO: 28)

wherein
X$_1$ is a polar or charged amino acid;
X$_2$ is a polar amino acid;
X$_3$ is a hydrophobic or amphipathic amino acid; and
X$_4$ is a hydrophobic, amphipathic, charged, or polar amino acid.

3. The scaffold peptide of claim 2, wherein the one or more GnRH peptides comprise amino acid sequence SEQ ID NO: 28, wherein X$_1$ is Q, E, or pE;
X$_2$ is Y or H;
X$_3$ is L or W; or
X$_4$ is L, Y, R, or Q.

4. The scaffold peptide of claim 1, wherein the one or more GnRH peptides comprise amino acid sequence:

```
                              (SEQ ID NO: 29)
    QHWSYGLRPG;

(SEQ ID NO: 30)
    QHWSHGWLPG;
```

```
                              (SEQ ID NO: 31)
    EHWSYGLRPG;

(SEQ ID NO: 32)
    QHWSYGWYPG;

(SEQ ID NO: 33)
    EHWSYGLQPG;
    or (SEQ ID NO: 34)
    QHWSHGWYPG.
```

5. The scaffold peptide of claim 1, wherein the scaffold peptide comprises two or more GnRH peptides and wherein the GnRH peptides are obtained from different sources and/or comprise two or more different amino acid sequences selected from SEQ ID NO: 28, 29, 30, 31, 32, 33, or 34.

6. The scaffold peptide of claim 1, wherein the scaffold peptide further comprises an immunomodulator or hapten, optionally wherein the immunomodulator or hapten is a T-cell epitope or a B-cell epitope.

7. The scaffold peptide of claim 1, wherein the scaffold peptide comprises amino acid sequence SEQ ID NO: 67 or 69.

8. A GnRH conjugate (GnRH-hC) or a GnRH oligomer (GhC) comprising one or more Gonadotropin releasing hormone (GnRH) peptides covalently attached to a hapten carrier (hC), the hC comprising an oligomer which comprises a monomeric peptide,
wherein the monomeric peptide comprises amino acid sequence SEQ ID NO: 3, 4, 5, 6, 7, 8, 9, 10, 11, 12, 13, 15, 16, 17, or 18; or
wherein the monomeric peptide comprises amino acid sequence SEQ ID NO: 19 20, 21, 22, 23, 24, 25, 26, or 27.

9. The conjugate or oligomer of claim 8, wherein the oligomer comprises a dimer, trimer, tetramer, pentamer, hexamer, heptamer, octamer, nanomer, or decamer.

10. The GnRH conjugate or GnRH oligomer of claim 8, wherein the one or more GnRH peptides comprise the amino acid sequence:

$$X_1HWSX_2GX_3X_4PG, \quad \text{(SEQ ID NO: 28)}$$

wherein

X$_1$ is a polar or charged amino acid;

X$_2$ is a polar amino acid;

X$_3$ is a hydrophobic or amphipathic amino acid; and

X$_4$ is a hydrophobic, amphipathic, charged, or polar amino acid.

11. The GnRH conjugate or GnRH oligomer of claim 8, wherein the one or more GnRH peptides comprise amino acid sequence SEQ ID NO: 28, wherein X$_1$ is Q, E, or pE;

X$_2$ is Y or H;

X$_3$ is L or W; or

X$_4$ is L, Y, R, or Q.

12. The GnRH conjugate or GnRH oligomer of claim 8, wherein the one or more GnRH peptides comprise amino acid sequence:

$$QHWSYGLRPG; \quad \text{(SEQ ID NO: 29)}$$

$$QHWSHGWLPG; \quad \text{(SEQ ID NO: 30)}$$

$$EHWSYGLRPG; \quad \text{(SEQ ID NO: 31)}$$

$$QHWSYGWYPG; \quad \text{(SEQ ID NO: 32)}$$

$$EHWSYGLQPG; \quad \text{(SEQ ID NO: 33)}$$
or $$QHWSHGWYPG. \quad \text{(SEQ ID NO: 34)}$$

13. The GnRH conjugate or GnRH oligomer of claim 8, wherein the GnRH conjugate or GnRH oligomer comprises two or more GnRH peptides and wherein the GnRH peptides are obtained from different sources and/or comprise different amino acid sequences selected from SEQ ID NO: 28, 29, 30, 31, 32, 33, or 34.

14. The GnRH conjugate or GnRH oligomer of claim 8, wherein the one or more GnRH peptides are conjugated to the hC through the y residue on the monomeric peptide.

15. The GnRH conjugate or GnRH oligomer of claim 8, wherein the GnRH conjugate or GnRH oligomer further comprises one or more immunomodulators or haptens, and optionally wherein the one or more haptens or immuno-modulators comprise GnRH peptide, one or more T-cell epitopes, and/or one or more B-cell epitopes.

16. The GnRH conjugate or GnRH oligomer of claim 8, wherein the GnRH conjugate or GnRH oligomer comprises one or more spacers between the hapten or immunomodu-lator and the monomeric peptide, and wherein the spacers comprise G (glycine), D (aspartic acid), S (serine), C (cys-teine), or a combination thereof.

17. The GnRH conjugate or GnRH oligomer of claim 15, wherein the one or more additional haptens or immuno-modulators comprise a lipid, a peptide, a nucleic acid, or a combination thereof, and wherein the one or more additional haptens or immunomodulators are conjugated to the hC or covalently attached at the one or more N-and/or C-terminus of the oligomer's helices.

18. The GnRH conjugate or GnRH oligomer of claim 8, wherein the GnRH conjugate or GnRH oligomer comprises a scaffold peptide including an amino acid sequence SEQ ID NO: 67, 68, or 69.

19. The GnRH conjugate or GnRH oligomer of claim 8, wherein the GnRH conjugate or GnRH oligomer comprises a peptide immunogen comprising amino acid sequence SEQ ID NO: 70 or SEQ ID NO: 71.

20. A composition comprising the peptide of claim 1 and an excipient, and optionally wherein the composition is a pharmaceutical composition and the excipient is a pharma-ceutically acceptable excipient.

21. A method of treating a subject having a disease wherein the method comprises administering to the subject in need thereof, an effective amount of the peptide of claim 1, wherein the hapten induces an immune response to treat the subject.

22. The method of of claim 21, wherein the disease is prostate cancer.

23. A composition comprising the GnRH conjugate or the GnRH oligomer of claim 8 and an excipient, and optionally wherein the composition is a pharmaceutical composition and the excipient is a pharmaceutically acceptable excipient.

24. A method of treating a subject having a disease, wherein the method comprises administering to the subject in need thereof, an effective amount of the GnRH conjugate or GnRH oligomer of claim 8, and wherein the hapten induces an immune response to treat the subject.

25. The method of any one of claim 24, wherein the disease is prostate cancer.

26. The peptide of claim 1, wherein:

the one or more GnRH peptides further comprise G, V, M, A, or a combination thereof at the N-and/or C-termi-nus; or the one or more GnRH peptides further comprise GEDC (SEQ ID NO: 36) or DGEGC (SEQ ID NO: 37) at the C-terminus.

27. The GnRH conjugate or GnRH oligomer of claim 8, wherein:

the one or more GnRH peptides further comprise G, V, M, A, or a combination thereof at the N-and/or C-termi-nus; or the one or more GnRH peptides further comprise GEDC (SEQ ID NO: 36) or DGEGC (SEQ ID NO: 37) at the C-terminus.

28. The GnRH conjugate or GnRH oligomer of claim 8, wherein the one or more haptens or immunomodulators comprise GnRH peptide, one or more T-cell epitopes, and/or one or more B-cell epitopes; and optionally, wherein the one or more T-cell epitopes comprise CD4+ T-cell epitopes.

29. The GnRH conjugate or GnRH oligomer of claim 28, wherein the GnRH conjugate or GnRH oligomer further comprises one or more residues for correct processing of the one or more T-cell epitopes.

30. The GnRH conjugate or GnRH oligomer of claim 16, wherein the one or more residues comprise D, G, P, S, GD, PGP, GSG, GPGP (SEQ ID NO: 63), GPGPG (SEQ ID NO: 64), GPGPGC (SEQ ID NO: 65), or SGPGPG (SEQ ID NO: 66).

31. The method of claim 21, wherein the subject is a mammal; and optionally, wherein the mammal is a human.

* * * * *